US009616052B2

(12) United States Patent
Dooley

(10) Patent No.: US 9,616,052 B2
(45) Date of Patent: *Apr. 11, 2017

(54) METHODS AND PHARMACEUTICAL COMPOSITIONS FOR THE TREATMENT OF SYMPTOMS OF ANXIETY AND PANIC USING BETA ADRENERGIC RECEPTOR ANTAGONIST AND MUSCARINIC RECEPTOR ANTAGONIST COMBINATIONS

(71) Applicant: Thomas P. Dooley, Pinson, AL (US)

(72) Inventor: Thomas P. Dooley, Pinson, AL (US)

(73) Assignee: Thomas P. Dooley, Pinson, AL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/345,896

(22) Filed: Nov. 8, 2016

(65) Prior Publication Data

US 2017/0049757 A1    Feb. 23, 2017

Related U.S. Application Data

(60) Continuation of application No. 14/803,434, filed on Jul. 20, 2015, now Pat. No. 9,517,231, which is a division of application No. 14/801,898, filed on Jul. 17, 2015, now Pat. No. 9,446,030.

(60) Provisional application No. 62/027,375, filed on Jul. 22, 2014, provisional application No. 62/052,600, filed on Sep. 19, 2014, provisional application No. 62/055,209, filed on Sep. 25, 2014.

(51) Int. Cl.

| | |
|---|---|
| *A61K 31/439* | (2006.01) |
| *A61K 31/165* | (2006.01) |
| *A61K 47/02* | (2006.01) |
| *A61K 47/20* | (2006.01) |
| *A61K 31/138* | (2006.01) |
| *A61K 47/10* | (2006.01) |
| *A61K 47/26* | (2006.01) |
| *A61K 31/46* | (2006.01) |
| *A61K 9/06* | (2006.01) |
| *A61K 9/20* | (2006.01) |
| *A61K 9/48* | (2006.01) |
| *A61K 9/107* | (2006.01) |
| *A61K 9/00* | (2006.01) |
| *A61K 9/02* | (2006.01) |

(52) U.S. Cl.

CPC ............ *A61K 31/439* (2013.01); *A61K 9/006* (2013.01); *A61K 9/0014* (2013.01); *A61K 9/0031* (2013.01); *A61K 9/0034* (2013.01); *A61K 9/0053* (2013.01); *A61K 9/02* (2013.01); *A61K 9/06* (2013.01); *A61K 9/107* (2013.01); *A61K 9/20* (2013.01); *A61K 9/48* (2013.01); *A61K 31/138* (2013.01); *A61K 31/165* (2013.01); *A61K 47/02* (2013.01); *A61K 47/10* (2013.01)

(58) Field of Classification Search

CPC .. A61K 31/439; A61K 31/138; A61K 31/165; A61K 47/10; A61K 47/20; A61K 47/26; A61K 47/02; A61K 9/0014; A61K 9/02; A61K 9/06; A61K 9/107; A61K 9/20; A61K 9/48; A61K 9/0031; A61K 9/0034; A61K 9/0053; A61K 9/006

USPC ....................................................... 514/291

See application file for complete search history.

(56) References Cited

U.S. PATENT DOCUMENTS

| | | | |
|---|---|---|---|
| 4,532,244 A | 7/1985 | Innes | |
| 4,755,386 A | 7/1988 | Hsiao et al. | |
| 5,798,393 A | 8/1998 | Swartz | |
| 8,012,503 B2 | 9/2011 | Chow | |
| 9,446,030 B2 * | 9/2016 | Dooley | ................ A61K 31/165 |
| 9,517,231 B2 * | 12/2016 | Dooley | ................ A61K 31/439 |
| 2009/0220611 A1 | 9/2009 | Dargelas | |
| 2011/0218215 A1 | 9/2011 | Holly | |
| 2011/0281853 A1 | 11/2011 | Arora et al. | |
| 2013/0116215 A1 | 5/2013 | Coma | |

FOREIGN PATENT DOCUMENTS

| | | |
|---|---|---|
| RU | 2 194 538 | 12/2002 |
| WO | WO 2006/127418 | 11/2006 |

(Continued)

OTHER PUBLICATIONS

Becker, A.L. "Oxprenolol and Propanolol in Anxiety States", South African Medical Journal, 50:627-629, 1976.

(Continued)

*Primary Examiner* — Kristin Vajda
(74) *Attorney, Agent, or Firm* — Hueschen and Sage

(57) ABSTRACT

The present invention is focused primarily toward pro re nata ("as needed") treatments for a psychiatric condition or disorder or the symptoms thereof, including the symptoms of acute anxiety and panic in living animals, including humans. The present invention encompasses pharmaceutical compositions as combination therapies containing at least one beta adrenergic receptor antagonist and at least one muscarinic receptor antagonist. The invention provides methods for treating psychiatric condition or disorder or the symptoms thereof, including acute anxiety and panic comprising administering a pharmaceutical composition consisting essentially of a beta adrenergic receptor antagonist drug and an antiemetic muscarinic receptor antagonist drug in a therapeutically effective amount to stop or reduce the symptoms of anxiety and/or panic. The pharmaceutical compositions are administered as treatments immediately in advance of, at the onset of, or during an acute anxiety and/or panic episode.

18 Claims, No Drawings

(56) References Cited

FOREIGN PATENT DOCUMENTS

| WO | WO 2011/143457 | 11/2011 |
|---|---|---|
| WO | WO 2012/071573 | 5/2012 |

OTHER PUBLICATIONS

Gottlieb, Louis, D,. et al, "Randomized controlled trial in alcohol relapse prevention: role of atenolol, alcohol craving, and treatment adherence", Journal of Substance Abuse Treatment, vol. 11 No. 3, 1994, pp. 253-258.
International Search Report and Written Opinion for PCT/US2015/014657, Apr. 28, 2015.
Kukkonen-Harjula, et al. "Cardiovascular effects of Atenolol, Scopolamine and their combination on healthy men in Finnish sauna baths", European Journal of Applied Physiology and Occupational Physiology, 69:10-15, 1994.
Llorca, et al. "Efficiacy and Safety of Hydrazine in the Treatment of Generalized Anxiety Discorder: A 3-Month Double-Blind Study", Journal of Clinical Psychiatry, 63:1020-1027, 2002.
Pitman, Roger, K., et al., "Pilot study of secondary prevention of posttraumatic stress disorder with propranolol", Biol Psychiatry, 51, 2002, pp. 189-192.
Vaiva, Guillaume, et al., "Immediate Treatment with propranolol decreases posttraumatic stress disorder two months after trauma", Biol Psychiatry, 52, 2003, pp. 947-949.
Alexander, Jessica, K., et al., "Beta-adrenergic modulation of cognitive flexibility during stress", Journal of Cognitive Neuroscience, 19:3, 2007, pp. 468-478.
Altamura, Alfredo, Carlo, et al., "Understanding the pharmacokinetics of anxiolytic drugs". Expert Opin. Drug Metab. Toxicol., 2013, pp. 1-18.
Anderws, Julie, et al., "The combined propranolol/TSST paradigm—a new method for psychoneuroendocrinology", PLoS One, vol. 8, Issue 2, e57567, Feb. 2013, pp. 1-8.
Andrade, Laura, et al., Lifetime comorbidity of panic attacks and major depression in a population-based study; Symptom profiles, British Journal of Psychiatry, 165, 1994, pp. 363-369.
Banerjee, M., "Propranolal in the treatment of Acute migraine attacks", Cephalalgia, vol. 11(4), Sep. 1991, pp. 193-196.
Bell, J., "Propranolol, post-traumatic stress disorder and narrative identity", J Med Ethics, 34, e23, 2008, pp. 1-4.
Beversdorf, David, Q., et al., "Central β-adrenergic modulation of cognitive flexibility", Cognitive Neuroscience and Neuropsychology, vol. 13, No. 18, Dec. 2002, pp. 2505-2507.
Bram, G., "An evaluation of tofenacine (alamoi), a new drug for the treatment of depression", Current Therapeutic Research Clin Exp., vol. 13, Issue, Oct. 10, 1971, pp. 625-630.
Brantigan, C.O., et al., "Effect of beta blockade and beta stimulation on stage fright", The American Journal of Medicine, vol. 72, Jan. 1982, pp. 88-94.
Breslau, N., et al., "Headaches types and panic disorder; Directionality and specificity", Neurology, 56, 2001, pp. 350-354.
Cahill, Shawn, P., "Posttraumatic stress disorder and acute stress disorder II: Considerations for treatment and prevention", Psychiatry, Sep. 2005, pp. 34-46.
Capstick, N., et al., "A comparative trial of orphenadrine and tofenacin in the control of depression and extrapyramidal side-effects associated with fluphenazine decanoate therapy", J Int Med Res, 4, 1976, pp. 435-440.
Cheng, Judy, W.M., "Nebivolol: A third-generation β-blocker for hypertension", Clinical Therapeutics, vol. 32, No. 3, 2009, pp. 447-462.
Chiam, Patrick, J. T., "Topical beta-blocker treatment for migraine", Int Ophthalmol, 32, 2012, pp. 85-88.
Corallo, Carmela, E., et al., "Anticholinergic syndrome following an unintentional overdose of scopolamine", Therapeutics and Clinical Risk Management, 5, 2009, pp. 719-723.

Diamond, Seymour, "Strategies for migraine management", Cleveland Clinic Journal of Medicine, May-Jun. 1991, pp. 257-261.
Disgranes, O., "Beta blocker treatment in aocohol withdrawal. A double-blind test with pindolol (Viskèn) placebo", T. Norske Lægeforen, 96, 1976, pp. 226-228.
Drevets, Wayne, C., "Replication of scopolamine's antidepressant efficacy in major depressive disorder: a randomized, placebo-controlled clinical trial", Biol Psychiatry, 67(5), Mar. 1, 2010, pp. 432-438.
Drew, P.J.T., et al., "The effect of acute β-adrenoceptor blockade on examination performance", Br. J. Clin. Pharmac., 19, 1985, pp. 783-786.
Duchateau, Guus, S.M.J.E, et al., "Bioavailability of propranolol after oral, sublingual, and intranasal administration", Pharmaceutical Research, vol. 3, No. 2, 1986, pp. 108-111.
Edvardsson, Bengt, "Atenolol in the prophylaxis of chronic migraine: a 3-month open-lable study", SpringerPlus, 2:479, 2013, pp. 1-5.
Ellis, M., "Cardioselectivity of atenolol in asthmatic patients", European Journal of Clinical Pharmacology, vol. 21, Issue 3, 1981, pp. 173-176.
Faigel, H., "The effect of beta blockade on stress-induced cognitive dysfunction in adolescents", Clinical Pediatrics, vol. 30, Issue 7, Jul. 1991, pp. 441-445.
Furey, Maura, L., et al., "Antidepressant efficacy in the antimuscarinic drug scopolamine: a randomized, placebo-controlled clinical trial", Arch Gen Psychiatry, 63(10), Oct. 2006, pp. 1121-1129.
Furey, Maura, L., et al., "Scopolamine produces larger antidepressant and antianxiety effects in women than in men", Neuropsychopharmacology, 35, 2010, pp. 2479-2488.
Gates, G., "Effect of beta blockade on signing performance", Annals of Otology, Rhinology & Laryngology, vol. 94, Issue 6, Nov. 1985, pp. 570-574.
Gillin, J., "The effects of scopolamine on sleep and mood in depressed patients with a history of alcoholism and a normal comparison group", Biological Psychiatry, vol. 30, Issue 2, Jul. 1991, pp. 157-169.
Gottlieb, Louis, D., et al., "Randomized controlled trial in alcohol relapse prevention: role of atenolol, alcohol craving, and treatment adherence", Journal of Substance Abuse Treatment, vol. 11, No. 3, 1994, pp. 253-258.
Gray, Melissa, Y., "The use of anticholinergics for the management of terminal secretions", Evidence Matters, 1(3), Summer 2007, pp. 1-6.
Greenblatt, David, J., "Pharmacokinetic comparison of sublingual lorazepam with intravenous, intramuscular, and oral lorazepam", Journal of Pharmaceutical Sciences, vol. 71(2), Feb. 1982, pp. 248-252.
Greenway, Frank, et al., "A clinical trial testing the safety and efficacy of a standardized Eucommia ulmoides oliver bark extract to treat hypertension", Alternative Medicine Review, vol. 16(4), 2011, pp. 338-347.
Gros, Daniel, F., "Psychometric properties of the state-trait inventory for cognitive and somatic anxiety (STICSA): Comparison to the state-trait anxiety inventory (STAI)", Psychological Assessment, vol. 19., No. 4, 2007, pp. 369-381.
Guaiana, G., et al., "Hydroxyzine for generalised anxiety disorder (Review)", The Cochrane Collaboration, Issue 12, 2010, pp. cover-79.
Hagan, John, C. & Migliazzo, Carl, V., "Are drops the 'solution'? A eureka moment? Beta blocker eye drops for acute migraines", Missouri Medicine, vol. 111, No. 4, Jul./Aug. 2014, pp. cover, 280-296.
Hanania, Nicola, A., "The safety and effects of the beta-blocker, nadolol, in mild asthma; an open-label pilot study", Pulm Pharmacol Ther., 21(1), 2008, pp. 134-141.
Hoge, Elizabeth, A., "Effect of acute posttrauma propranolol on PTSD outcome and physiological responses during script-driven imagery", CNS Neuroscience & Therapeutics, 18, 2012, pp. 21-27.
Holroyd, Kenneth, A., "Effect of preventive (βblocker) treatment, behavioural migraine management, or their combination on out-

(56) References Cited

OTHER PUBLICATIONS comes of optimised acute treatment in frequent migraine: randomised Controlled trial", BMJ, 341:c4871, 2010, pp. 1-12.
Horwitz, R., "The efficacy of atenolol in the outpatient management of the alcohol withdrawal syndrome, Results of a randomized clinical trial", Archives of Internal Medicine, vol. 149(5), May 1989, pp. 1089-1093.
Houde, A., "Scopolamine: A physiological and clinical study", Gleanings from Foreign Fields, Revue Therapeutique des Alcaloids, Nov. 1905.
Imai, Kengo, et al., "Sublingually administered scopolamine for nausea in terminally ill cancer patients", Support Care Cancer, 21, 2013, pp. 2777-2781.
Iskandar, Joseph, W., et al., "Successful treatment with hydroxyzine of acute exacerbation of panic disorder in a healthy man: a case report", Prim Care Companion CNS Disord, 13(3), 2011, pp. 1-2.
James, I., "Beneficial effect of nadolol on anxiety-induced disturbances of performance in musicians: a comparison with diazepam and placebo", Am Heart J., vol. 108(4 Pt 2), Oct. 1984, pp. 1150-1155.
James, I.M., et al., "Effect of pindolol on stress-related disturbances of musical performance: preliminary communication", Journal of the Royal Society of Medicine, vol. 76, Mar. 1983, pp. 194-196.
Kampman, Kyle, M., et al., "A double-blind, placebo-controlled trial of amantadine, propranolol, and their combination for the treatment of cocaine dependence in patients with severe cocaine withdrawal symptoms", Drug and Alcohol Dependence, 85, 2006: pp. 129-137.
Kampman, Kyle, M., et al., "Effectiveness of propranolol for cocaine dependence treatment may depend on cocaine withdrawal symptom severity", Drug and Alcohol Dependence, 63, 2001, pp. 69-78.
Kellner, Michael, "Experimental panic provocation in healthy man—a translational role in anti-panic drug development", Dialogues Clin Neurosci., 13, 2011, pp. 485-493.
Kessler, Ronald, C., et al., "Lifetime prevalence and age-of-onset distributions of DSM-IV disorders in the national comorbidity survey replication", Arch Gen Psychiatry, 62, 2005, pp. 593-602.
Kessler, Ronald, C., et al., "Prevalence, severity, and comorbidity of twelve-month DSM-IV disorders in the national comorbidity survey replication (NCSR)", Arch Gen Psychiatry, 62(6), Jun. 2005, pp. 617-627.
Kessler, Ronald, C., et al., "The epidemiology of panic attacks, panic disorder, and agoraphobia in the national comorbidity survey replication", Arch Gen Psychiatry, 63(4), Apr. 2006, pp. 415-424.
Khajavi, Danial, et al., "Oral scopolamine augmentation in moderate to severe major depressive disorder: a randomized, double-blind, placebo-controlled study", J. Clin Psyciatry, 73(11), 2012, pp. 1428-1433.
Koller, W., "Effect of alcohol on tremors:comparison with propranolol", Neurology, vol. 34(2), Feb. 1984, pp. 221-222.
Kraus, M., "Randomized clinical trial of atenolol in patients with alcohol withdrawal", New England Journal of Medicine, 313(15), Oct. 1985, pp. 905-909.
Kronenberg, G., et al "In healthy volunteers responses to challenge with cholecystokinin tetrapeptide differ between administration REM and Delta sleep", Depression and Anxiety, 14, 2001, pp. 141-144.
Kudielka, Brigitte, M., et al., "No effect of 5-day treatment with Acetylsallcyclic acid (aspirin) or the beta-blocker propranolol (Inderal) on free cortisol responses to acute pshychosocial stress: a randomized double-blind, placebo-controlled study", Neuropsychobiology, 56, 2007, pp. 159-166.
Lader, M., "Beta-adrenoceptor antagonists in neuropsychiatry: an update", J. Clin Psychiatry, vol. 49(6), Jun. 1988, pp. 213-223.
Loder, Elizabeth, et al., "The 2012 AHS/AAN guidelines for prevention of episodic migraine: a summary and comparison with other recent clinical practice guidelines", Headache, 52, 2012, pp. 930-945.
MacKinnon, Dean, F., et al., "Carbon dioxide provocation of anxiety response in bipolar disorder", J Affect Disord., 99(1-3), Apr. 2007, pp. 45-49.
Mansur, A.P., et al., "Pharmacokinetics and pharmacodynamics of propranolol in hypertensive patients after sublingual administration: systemic availability", Brazilian Journal of Medical Research, 31, 1998, pp. 691-696.
Marazziti, D., "Prevalence of headache syndromes in panic disorder", International Clinical Psychopharmacology, Vo. 14, issue 4, Jul. 1999, pp. 247-251.
Marteau, Theresa, M., et al., "The development of six-item short-form of the state scale of the Spielberger state-trait anxiety inventory (STAI)", British Journal of Clinical Psychology, 31, 1992, pp. 301-306.
McGhee, Laura, L, et al., "The effect of propranolol on post-traumatic stress disorder in burned service members", J Burn Care Res, 30, 2009, pp. 92-97.
Morimoto, K., "Design of polyvinyl alcohol hydrogel as a controlled-release vehicle for rectal administration of dl-propranolol-HCI and atenolol", Chemical & Pharmaceutical Bulletin, vol. 37(9), Sep. 1989, pp. 2491-2495.
Munjack, D., "Alprazolam, propranolol, and placebo in the treatment of panic disorder and agoraphobia with panic attacks", J Clin Psychopharmacol, 9(1), Feb. 1989, pp. 22-27.
Nachum, Zohar, et al., "Transdermal scopolamine for prevention of motion sickness, Clinical pharmacokinetics and therapeutic applications", Clin. Pharmacokinet, 45(6), 2006, pp. 543-566.
Navas, Elsy, Viviana, et al., "Can patients with COPD or asthma take a beta-blocker"?, Cleveland Clinic Journal of Medicine, vol. 77, No. 8, Aug. 2010, pp. 498-499.
Neftel: Klaus, A., et al., "Stage fright in musicians, a model illustrating the effect of beta blockers", Psychosomatic Medicine, vol. 44, No. 5, Nov. 1982, pp. 461-469.
Onuaguluchi, G., "Assessment of drug therapy in Parkinsonism", British Medical Journal, Feb. 16, 1963, pp. 443-448.
Papadopoulos, A., et al., "The effects of single dose anxiolytic medication on the CO2 models of anxiety: differentiation of subjective and objective measures", Journal of Psychopharmacology, 24(5), 2010, pp. 649-656.
Pessina, Achille, C., "Metabolic effects and safety profile of nebivolol", Journal of Cardiovascular Pharmacology, 38 (Suppl. 3), 2001, pp. S33-S35.
Pitman, Roger, K., et al., "Pilot study of secondary prevention of posttraumatic stress disorder with propranolol", Biol Psychiatry, 51, 2002, pp. 189-142.
Plotnik, R., "Comparing the effects of scopolamine on operant and aggressive responses in squirrel monkeys", Pharmacology, Biochemistry, and Behavior, vol. 3(5), Sep. 1975, pp. 739-748.
Potter, J., "The effect of a non-selective lipophilic beta-blocker on the blood pressure and noradrenaline, vasopressin, cortisol and renin release during alcohol withdrawal", Clinical and Experimental Hypertension, Part A, Theory and Practice, vol. 6(6), 1984, pp. 1147-1160.
Ravaris, C., "A controlled study of alprazolam and propanolol in panic-disordered and agoraphobic outpatients", J Clin Psychopharmacol., 11(6), Dec. 1991, pp. 344-350.
Schellenberg, Rudiger, et al., "Nebivolol and metoprolol for treating migraine: an advance on β-blocker treatment", Headache, 48, 2008, pp. 118-125.
Schneier, Franklin, R., "Social anxiety disorder", N Engl J Med, 355, 2006, pp. 1029-1036.
Shamliyan, Tatyana, A, et al., "Episodic migraines in children: limited evidence on preventive pharmacological treatments", Journal of Child Neurology, 28(10), 2013, pp. 1320-1341.
Silver, Jennifer, A., et al., "Effect of anxiolytics on cognitive flexibility in problems solving", Cog Behav Neurol, vol. 17, No. 2, Jun. 2004, pp. 93-97.
Silver, Johnathan, M., "Propranolol treatment of chronically hospitalized aggressive patients", J Neuropsychiatry Clin Neurosci, 11, 1999, pp. 328-335.
Smitherman, Todd, A., et al., "Panic disorder and migraine: comorbidity, mechanism, and clinical implications", Headache, 53, 2013, pp. 23-45.

(56) References Cited

OTHER PUBLICATIONS

Smitherman, Todd, A., et al., "The prevalence, impact, and treatment of migraine and severe headaches in the United States: a review of statistics from national surveillance studies", Headache, 53, 2013, pp. 427-436.

Stein, Murray, B., et al., "Pharmacotherapy to prevent PTSD: results from a randomized controlled proof-of-concept trial in physically injured patients", Journal of Traumatic Stress, vol. 20, No. 6, Dec. 2007, pp. 923-932.

Ströhle, Andreas, et al., "Effect of flumazenil in lactate-sensitive patients with panic disorder", Am J Psychiatry, 155, 1998, pp. 610-612.

Tyrer, P.J., et al., "Physiological response to propranolol and diazepam in chronic anxiety", Br. J. Clin. Pharmac., 1, 1974, pp. 387-390.

Tyrer, P.J., et al., "Response to propranolol and diazepam in somatic and psychic anxiety", British Medical Journal, 2, 1974, pp. 14-16.

Vaiva, Guillaume, et al., "Immediate treatment with propranolol decreases posttraumatic stress disorder two months after trauma", Biol Psychiatry, 54, 2003, pp. 947-949.

von Känel, Roland, et al., "Aspirin, but not propranolol, attenuates the acute stress-induced increase in circulating levels of interleukin-6: a randomized, double-blind, placebo-controlled study", Brain, Behavior, and Immunity, 22, 2008, pp. 150-157.

Wang, Jen, C., et al., "Evidence of common and specific genetic effects: association of the muscarinic acetylcholine receptor M2 (CHRM2) gene with alcohol dependence and major depressive syndrome", Human Molecular Genetics, vol. 18, No. 17, 2004, pp. 1903-1911.

Wang, Philip, S., et al., "Twelve-month use of mental health services in the United States", Arch Gen Psychiatry, 62, 2005, pp. 629-640.

Wang, Yanfeng, et al., "Clinical pharmacokinetics of buffered propranolol sublingual tablet (Promptol™)-application of a new "physiologically based" model to assess absorption and disposition", The AAPS Journal, Apr. 19, 2013, pp. 1-10.

Witkin, J.M., et al., "M1 and M2 muscarinic receptor subtypes regulate antidepressant-like effects of the rapidly acting antidepressant scopolamine", J Pharmacol Exp Ther, 351, Nov. 2014, pp. 448-456.

Yamada, Kazuo, et al., "High prevalence of comorbidity of migraine in outpatients with panic disorder and effectiveness of psychopharmacotherapy for both disorders: a retrospective open label study", Psychiatry Research, 185, 2011, pp. 145-148.

Zamorski, Mark, A., et al., "What to do when SSRIs fail: eight strategies for optimizing treatment of panic disorder", American Family Physician, vol. 66, No. 8, Oct. 15, 2002, pp. 1477-1484.

Zervakis, Jennifer, et al., "Taste effects of lingual application of cardiovascular medications", Physiology & Behavior, 68, 2000, pp. 405-413.

\* cited by examiner

METHODS AND PHARMACEUTICAL COMPOSITIONS FOR THE TREATMENT OF SYMPTOMS OF ANXIETY AND PANIC USING BETA ADRENERGIC RECEPTOR ANTAGONIST AND MUSCARINIC RECEPTOR ANTAGONIST COMBINATIONS

BACKGROUND OF THE INVENTION

In spite of the abundance and availability of numerous oral psychiatric pharmaceuticals, there is an unmet need in the pharmaceutical marketplace for fast-acting therapies for the pro re nata (p.r.n.; "as needed") treatment of symptoms of acute anxiety and panic. The present invention addresses multiple aspects of this unmet medical need via the following beneficial features, among others.

The present invention is focused primarily toward p.r.n. treatments for the symptoms of acute anxiety and panic. The same or similar treatments may also provide benefit with regard to an even broader group of psychiatric conditions or disorders, such as alcohol addiction and/or withdrawal, drug addiction and/or withdrawal, migraine, headache, and aggression. Effective treatments for the symptoms of acute anxiety and panic per se should coincidentally reduce or remove some of the same somatic and/or psychic symptoms associated with this broader group of psychiatric conditions.

The active pharmaceutical ingredient (API) combinations of the present invention provide complementary pharmacologic benefits by interaction of two types of APIs having two (or more) dissimilar pharmacologic molecular targets. The biochemical pathways of the beta adrenergic receptor and muscarinic receptor gene families are appropriate anxiolytic targets for the symptoms of panic attack (PA), panic disorder (PD), agoraphobia, generalized anxiety disorder, social anxiety disorder (social phobia), performance anxiety (e.g., stage fright), post-traumatic stress, post-traumatic stress disorder (PTSD), post-traumatic anxiety, and shell shock. These anxiety disorders are further delineated within the Diagnostic and Statistical Manual of Mental Disorders (e.g., DSM-5). Furthermore, these distinct biochemical pathways may be appropriate for therapeutic intervention for drug addiction and/or withdrawal, alcohol addiction and/or withdrawal, migraine, headache, and aggression. Those molecular targets can be components of the central nervous system (CNS), the peripheral nervous system, and/or of target somatic tissues (e.g., cardiovascular and gastrointestinal tissues). The appropriate combination of APIs is expected to affect more molecular targets than could be achieved by using a single API alone. Given that the multiplicity of symptoms of PA, PD, anxiety, and anxiety-related disorders are under the regulation of different neurologic, neuroendocrine, and endocrine pathways, it follows that pharmacologic antagonists affecting both the beta adrenergic receptors and muscarinic receptors could suppress more symptoms than could be achieved by a single API alone.

An acute anxiety or panic attack "trigger" circumstance results in the autonomic release of epinephrine (adrenaline), as well as cortisol and norepinephrine. This in turn causes multiple effects consistent with a "fight-or-flight response". Symptoms include tachycardia (increased heart rate), palpitations (perception of an elevated heart rate and/or of a strong heart beat), hypertension (increased blood pressure), hyperventilation (with reduced blood $CO_2$ and altered pH), dyspnea, mental anxiety, nausea, vomiting, fear, avoidance, trembling (tremors), sweating, headache, among others. Many of the somatic and/or psychic (CNS) symptoms of panic attack are shared in common with social anxiety disorder (social phobia), generalized anxiety disorder, agoraphobia, and PTSD. Therefore, it follows that an effective treatment for the symptoms of panic per se can also be effective against anxiety and anxiety-related disorders.

Some patients anticipate future episodes of panic or acute anxiety based upon his/her history of encounters with a known "trigger" circumstance. A trigger circumstance might be public speaking, a public music performance, flying, driving, a noise, a crowd of people (e.g., agoraphobia), decision-making, an unfamiliar setting, among others. Given the patients' anticipation of a trigger leading toward likely future symptoms, p.r.n. drug treatments of the present invention can be designed for rapid effect, and with the pharmacologic benefits beginning either during or immediately prior to the time when symptoms would be expected to commence.

The lifetime prevalence of PA is 28.3% of the adult US population [1]. The 12-month prevalence of panic disorder (PD) is estimated to be 2.7% of the adult US population [2], with 1.2% considered as "severe" [3]. More than half of affected adults (59.1% or ~3.8 million) are receiving treatment(s) [4]. Patients affected by PAs are often also affected by the co-morbid conditions of depression [5] and migraines (and other forms of headaches) [6, 7]. In aggregate panic and anxiety are extremely common, affecting nearly 40 million in the US.

The current standards-of-care for PD are oral psychiatric prophylactic pharmaceuticals, including: (1) Selective serotonin reuptake inhibitors (SSRIs), which are considered as the first choice medicines for PD. Examples include Paroxetine (PAXIL®), Sertraline (ZOLOFT®), and Fluoxetine (PROZAC®); (2) Benzodiazepines, such as Clonazepam (KLONOPIN®), Alprazolam (XANAX®), Lorazepam (ATIVAN®), and Diazepam (VALIUM®); (3) Serotonin-norepinephrine reuptake inhibitors (SNRIs), such as Duloxetine (CYMBALTA®) and Venlafaxine (EFFEXOR®); and (4) other medications, such as Quetiapine (SEROQUEL®), an antipsychotic prescribed for generalized anxiety disorder. These oral therapies are taken daily for the prevention of panic attacks. Some of these drugs are FDA approved for the prophylaxis of PD, such as Paroxetine, Sertraline, Alprazolam, and Clonazepam.

Other anxiety-related disorders are also treated in the same or a similar manner. For instance, social anxiety disorder (social phobia), generalized anxiety disorder, agoraphobia, and post-traumatic stress disorder (PTSD) are also treated using the same or similar oral daily pharmaceutical regimens [8].

The pharmaceutical standards-of-care in routine psychiatric care of PA, PD, anxiety, and anxiety-related disorders involve two key aspects: (1) prophylaxis, rather than treatment of the symptoms per se; and (2) the medications are routinely given as daily oral "maintenance" medications for persistent use (i.e., chronic prophylaxis), rather than as occasional administration "as needed" (p.r.n.) at the time of episodes of symptoms (i.e., acute therapy). The present invention provides an alternative paradigm that goes beyond the current standards-of-care in psychiatric medicine for PA, PD, anxiety, and anxiety-related disorders.

Although oral benzodiazepines have been used as persistent daily medications for the prophylaxis of panic and acute anxiety, they are not reasonable candidates for this alternative "fast-acting" p.r.n. approach of the present invention. Although benzodiazepines are often mistakenly considered to be "fast-acting", multiple clinical reports indicate otherwise. Zamorski and Albucher stated, "Benzodiazepines should not be used on an as-needed basis for panic disorder.

None of the oral benzodiazepines works quickly enough to affect any but the most prolonged panic attacks." [9] Altamura and coworkers stated recently, " . . . it would be desirable for the development of new anxiolytic drug(s) that are more selective, fast acting and free from the unwanted effects associated with the traditional benzodiazepines as tolerance or dependence." [10] Altamura and coworkers also stated regarding benzodiazepines as a class of anxiolytic drugs, "Only lorazepam is currently available in a form suitable for sublingual administration, which was developed in the hope that, by bypassing the gut, a more rapid onset could be achieved similar to that with intramuscular administration. However, Greenblatt et al. [11] found that the sublingual formulation was absorbed at a rate that did not differ significantly from that of regular oral administration of the standard tablets or even from that of sublingual administration of the standard oral tablets." [10] Thus, benzodiazepines are not suitable for rapid treatment of symptoms of panic attacks or acute anxiety episodes, even when delivered sublingually (mucosally). In conclusion, when "time is of the essence" for therapy, benzodiazepines are inadequate, regardless of the oral or sublingual routes of administration.

Furthermore, SSRIs are considered as the first choice medications for PD prophylaxis, but they require a very slow dose-escalation approach over weeks of time to produce a beneficial effect. Thus, the most common drugs for the indications that are the focus of this invention—benzodiazepines and SSRIs—are not feasible for p.r.n. therapy for rapid symptomatic relief.

Benzodiazepine and SSRI drugs can produce disabling psychic and somatic side effects, such as sedation, lethargy, chemical dependence, tolerance, and sexual dysfunction [9]. As a result of these negative side effects and potential for abuse, benzodiazepines are classified by the U.S. Food and Drug Administration (FDA) as Schedule 4 (IV) "Controlled Substances". Many physicians and other prescribers (e.g., dentists) are reluctant or prohibited from prescribing benzodiazepines. The present invention does not include either benzodiazepines or SSRIs as APIs. None of the APIs of the present invention are "Controlled Substances" as classified by the U.S. FDA Schedules 1-4.

The present invention encompasses pharmaceutical compositions as combination therapies containing at least one beta adrenergic receptor antagonist (e.g., propranolol, atenolol, or nadolol) and at least one muscarinic receptor antagonist (e.g., scopolamine, diphenhydramine, or meclizine). In an embodiment, a representative combination therapy of interest includes two well-known APIs, scopolamine and a beta blocker, such as propranolol.

Coma et al. (US Application Publication No. 2013/0116215) describe combinations of compounds which are therapeutically effective for treating neurodegenerative disorders. The application refers in general to methods of a "Therapeutic Performance Mapping System" technology. The application does not specifically disclose a combination of propranolol and scopolamine for the treatment of neurodegenerative diseases. Moreover, the application does not relate to the treatment of PA and PD.

Dargelas et al. (US Application Publication No. 2009/0220611) disclose microparticulate systems with modified release of oral active principle(s). The application explains that "coated 'reservoir' microparticles" may be used in the treatment of a lengthy list of medical indications, including cardiovascular and nervous system conditions among others, and discloses a lengthy list of APIs, for example, scopolamine or propranolol, which may be coated and formulated as microparticles.

Arora et al. (US Application Publication No. 2011/0281853) and Zembower & Arora (PCT International Publication No. WO 2011/143457) disclose compositions and methods for treating or preventing atrial fibrillation (AF). In particular, the application discloses administration of muscarinic receptor antagonists (e.g., M2-selective muscarinic receptor blockers), alone or in combination with other therapeutic agents (e.g., beta adrenergic receptor blockers), to treat and/or prevent atrial fibrillation. Arora et al. are silent with respect to compositions and methods for treating symptoms associated with PA, PD, anxiety, anxiety-related disorders, or psychiatry in general.

Kukkonen-Harjula and coworkers [12] discloses the cardiovascular effects of oral atenolol, oral scopolamine, or a coincident administration of both drugs in healthy volunteers prior to and during exposure to heat within a sauna. However, this article does not address pharmaceutical compositions and methods for treating PA, PD, anxiety, anxiety-related disorders, or psychiatry in general.

Frenette et al. (PCT International Publication No. WO2012/071573) disclose the use of beta adrenergic receptor antagonists (e.g., propranolol) and muscarinic receptor antagonists (e.g., scopolamine) among a lengthy list of APIs for use as cancer chemotherapies, specifically to inhibit tumor initiation and tumor metastasis.

Holly (US Application Publication No. 2011/0218215) discloses compositions and methods for treating social anxiety including a beta adrenergic receptor antagonist (specifically propranolol) coupled with an antidiarrheal agent (specifically the opioid diphenoxylate). The compositions may optionally include an anticholinergic agent (specifically atropine sulfate), but this is not required. And, the anticholinergic, atropine, is intended to deter abuse in the event of an overdose, rather than an efficacious benefit toward social anxiety. Unlike Holly, the present invention requires the inclusion of an anticholinergic agent, and does not require or envision an antidiarrheal agent. Furthermore, Holly is not directed toward PA or PD as therapeutic indications.

Chow et al. (U.S. Pat. No. 8,012,503) claim a method for enhancing absorption involving a mathematical calculation to derive a theoretical pH for a single API intended for administration to the oral mucosa. Scopolamine and propranolol are disclosed in a lengthy list of APIs for which a theoretical pH may be derived according to the mathematical calculation of the invention.

Hsiao et al. (U.S. Pat. No. 4,755,386) disclose a buccal-adhesive drug delivery technology. Both propranolol and scopolamine are included in a lengthy list of APIs, which may be included as single agents in the buccally-delivered adhesive composition of the invention.

The present invention is focused primarily on fast-acting, mucosally- and orally-delivered pharmaceutical compositions for p.r.n. ("as needed") treatment of symptoms of panic and acute anxiety, or in anticipation of the symptoms in patients. The compositions consist essentially of an antiemetic antimuscarinic drug and a beta adrenergic receptor antagonist drug, wherein the antimuscarinic drug may be scopolamine and the beta adrenergic receptor antagonist drug may be atenolol, propranolol, pindolol, nadolol, or nebivolol, among other choices.

The present invention is focused on the augmentation of a beta blocker's effects on the cardiovascular system's symptoms of acute anxiety or panic with an antiemetic antimuscarinic agent's effects on non-cardiovascular symptoms of acute anxiety or panic. The term "anxiety" covers a vast breadth of definitions and symptoms. The present invention addresses all or most of the symptoms of acute anxiety or panic episodes, neither of which is addressed by an "off-label" beta blocker alone or an antiemetic antimuscarinic agent alone. The present invention can achieve desirable pharmacologic effects upon a diverse array of cardiovascular and non-cardiovascular symptoms at appropriate doses of APIs that are antiemetic, non-sedating, fast-acting, and coincidentally without the use of addictive drugs and/or Controlled Substances as APIs. Furthermore, augmentation of a beta blocker (i.e., cardiovascular effects) with an antiemetic agent that only affects the symptoms of nausea, vomiting, and/or motion sickness per se provides anxiolytic superiority over a beta blocker alone or an antiemetic agent alone.

Propranolol is the most thoroughly studied of the beta blockers, and serves as the prototype for this class of drugs. Propranolol (or a pharmaceutically acceptable salt thereof) is a beta adrenergic receptor antagonist to reduce cardiac symptoms (e.g., tachycardia and hypertension) resulting from epinephrine in the circulation. Beta blockers interfere with receptor binding by catecholamines, epinephrine and norepinephrine, of which epinephrine is the principal catecholamine affecting the cardiac symptoms. Propranolol is a lipophilic beta blocker that readily crosses the blood-brain barrier. Therefore, it affects both somatic and CNS target tissues. Propranolol can be absorbed mucosally, as demonstrated by sublingual delivery [13], and its bioavailability is higher when absorbed by this route rather than orally [14, 15]. Also, propranolol has been delivered by rectal administration in mammals [16]. It does not demonstrate chemical dependence or sedation that are common side effects of many psychiatric medications.

Propranolol is prescribed for the treatment of various cardiovascular indications (with U.S. FDA approval), most notably hypertension, arrhythmia, angina, as well as prophylaxis of migraines. However, there is some evidence that it might also have some benefit with regard to a subset of the symptoms of panic and acute anxiety, although this is disputed. The drug's anxiolytic potential was recognized as early as 1966, "Emotions are expressed through the autonomic nervous system, and anxiety states are associated with increased secretion of catecholamines. Propranolol may therefore have a place in the treatment of anxiety, especially when the symptoms are related to the cardiovascular system." [17] This prescient comment five decades ago was subsequently validated by clinical studies with regard to both aspects: (a) propranolol and other beta blockers have been used off-label in the USA for the prophylaxis of performance anxiety; and (b) the pharmacologic benefits of propranolol and other beta blockers are restricted to the cardiovascular system effects per se. The beneficial anxiolytic effects are limited to blocking the pharmacologic effects of catecholamines upon the cardiovascular system without addressing the psychic (CNS) symptoms or other somatic symptoms of acute anxiety and panic, with the possible exception of tremors.

Daily oral propranolol has been demonstrated in one prophylactic study to suppress panic attacks in subjects diagnosed with panic disorder and agoraphobia [18]. Tyrer and Lader demonstrated some effectiveness of oral propranolol in treating somatic anxiety symptoms, but not psychic (mental) anxiety [19, 20]. Another daily oral prophylactic study compared propranolol to oxprenolol and revealed that both beta blockers reduced symptoms of anxiety at one or two weeks duration [21]. However, propranolol was more effective at reducing palpitations when assessed on day 7 compared to oxprenolol. In another clinical study, daily oral propranolol was not effective at treating panic disorder and agoraphobia with panic attacks [22].

There is some evidence suggesting that propranolol might be beneficial in academic test-taking among normal and anxiety-prone students. Examination performance might be increased by pretreatment with this beta blocker [23, 24].

Propranolol has been further studied in clinical trials designed to provoke anxiety. Using the Trier Social Stress Test (TSST) to provoke anxiety in a clinical setting, the somatic and psychic effects of oral propranolol were tested in healthy adult volunteers [25-28]. Propranolol (40 mg) one hour prior to TSST significantly reduced heart rate, reduced systolic blood pressure, and enhanced cognitive flexibility during stress [26]. In another study, propranolol (80 mg) one hour prior to TSST significantly reduced heart rate and increased salivary cortisol, but did not significantly affect BP or subjective stress [25]. In another TSST study, daily oral propranolol (80 mg) did not affect the salivary cortisol response [27]. In a study with healthy volunteer subjects using carbon dioxide inhalation to provoke panic and anxiety, propranolol significantly decreased heart rate, a somatic symptom, but did not provide psychic anxiolytic benefit [29].

Propranolol has also been investigated in patients suffering from severe posttraumatic stress disorder (PTSD). Two clinical studies of this beta blocker have shown possible benefits in the early-stage interventional prevention and subsequent therapy of PTSD [30, 31]. Subsequent reports have also echoed that propranolol might be effective for this condition [32-34], although other reports dispute this conclusion [35, 36].

When considered in aggregate these clinical studies of propranolol, as a well known prototypical beta blocker, provide convincing evidence that the drug can exert somatic (i.e., peripheral) effects on the cardiovascular system in the context of panic and anxiety. With regard to affecting the psychic (CNS) symptoms, the results have been negative, inconsistent, or inconclusive. That being said, there is some limited evidence that propranolol can exert some psychic (CNS) benefits in clinical stress trials. In a pair of clinical studies, propranolol (a central and peripheral beta-blocker) significantly enhanced problem solving during stress, whereas nadolol (peripheral only beta-blocker) and lorezapam (benzodiazepine) did not [37, 38]. Thus, propranolol enhanced cognitive flexibility ("creativity") during stress. It remains unclear whether propranolol alone can appreciably reduce psychic stress, thus the "need" to complement it with a dissimilar class of pharmacologic agents (e.g., muscarinic receptor antagonists). Thus, augmentation of a beta blocker's limited scope of effects upon the diversity of symptoms of acute anxiety and panic by another pharmacologic class of agents (i.e., antimuscarinic agents) is an essential aspect of the present invention.

The designs of many, if not all, of these historic clinical studies of propranolol might not mirror the conditions of the intended use of the present invention.

Numerous alternative beta blockers are available in lieu of propranolol, for instance atenolol, nadolol, pindolol, and nebivolol, among other choices. One appealing alternative beta blocker is atenolol that has been used to suppress stage fright in performers when administered orally in advance [39]. Atenolol is a beta-1 selective peripheral-acting agent without CNS effects, which should reduce the risk for asthmatic subjects [40]. Oral atenolol at 50-200 mg doses suppresses heart rate by ~23-24 beats per minute (bpm) vs. ~10 bpm on placebo [40]. Also, atenolol has been delivered by a mucosal route in mammals [16]. Plus, it was determined during development that sublingual formulations of the present invention containing atenolol do not have a taste and do not produce mouth paresthesia in humans. The latter two properties are unanticipated advantages over the use of propranolol in sublingual dose forms.

Another alternative beta blocker is nadolol, which is non-selective with a preference for beta-1 receptors, and does not pass through the blood-brain barrier. In a clinical trial with musicians, nadolol reduced pulse rate and improved one aspect of performance related to tremor [41]. A similar result was obtained for nadolol in students' singing performance [42]. In spite of being non-selective, nadolol might ironically benefit asthma patients based upon the appropriate dosage, an anti-intuitive result [43].

Another alternative is pindolol, another non-selective beta blocker, which can enhance the effects of co-administered antidepressants and has some 5-HT antagonist property. Pindolol reduced symptoms of performance anxiety in musicians [44].

Another alternative is nebivolol, a third-generation beta blocker. In view of its high degree of beta-1 selectivity, its reduced effect on the airways makes it appealing for patients with chronic obstructive pulmonary disease (COPD) and asthma [45, 46]. Thus, either nebivolol or atenolol might be preferred over the nonselective beta blockers for patients affected by asthma or COPD [47].

Another alternative is betaxolol. Swartz (U.S. Pat. No. 5,798,393) discloses daily oral betaxalol in the treatment of Generalized Anxiety Disorder, PD, and other anxiety-related conditions, stating that "Betaxalol works in 1 to 3 days . . . ." This anxiolytic benefit is prophylactic, as the effects are observed in days, rather than in minutes or hours.

In addition to the already known beta blockers, one can envision a medicinal chemistry approach to develop a structure-activity relationship (SAR) series of cardio-selective compounds (analogs or derivatives) related to beta blockers and/or their active metabolites in vivo, which could be beneficial APIs for compositions of the present invention.

Although the FDA-approved beta blockers are synthetic chemicals, a natural product extract of *Eucommia* bark and leaves has also been shown to have beta adrenergic receptor antagonist properties [48]. The active ingredients of this Asian herbal extract have not been characterized. This material provides another distinct advantage to the present invention; an over-the-counter (OTC) anxiolytic pharmaceutical composition for acute anxiety or panic could be produced that contains the natural product extract of *Eucommia* in combination with an OTC antiemetic muscarinic receptor antagonist. Depending on the choice of country, suitable and available OTC antiemetic antimuscarinic agents include diphenhydramine, orphenadrine, doxylamine, meclizine, buclizine, cyclizine, and scopolamine. Thus, dual drug combinations could be used as OTC drug products in certain international markets.

In view of the clinical studies and off-label use of beta blockers, most, if not all psychiatrists are aware that beta blockers can provide some symptomatic relief with regard to performance anxiety [49]. However, many psychiatrists are aware that beta blockers alone do not sufficiently address the aggregate symptoms of panic and acute anxiety, and especially the psychic symptoms thereof (e.g., fear, avoidance, and mental anxiety). Thus, there is a need to couple a beta blocker with another type of active ingredient. This is an essential aspect of the present invention.

Scopolamine (or a pharmaceutically acceptable salt thereof) is a plant-derived natural product that is commonly used for the treatment of motion sickness, nausea, and vomiting. The mechanism of action of this antiemetic drug is as an antagonist of muscarinic acetylcholine receptors. It is a nonselective muscarinic receptor inhibitor that can inhibit all five human receptor subtypes with ~0.34-5.3 nM $K_i$ values [50]. It is lipophilic and crosses the blood-brain barrier to exert psychic (CNS) pharmacologic effects. Scopolamine (or salt derivatives) is sold by prescription in the USA as a transdermal patch (TRANSDERM SCOP®) [51]. However, scopolamine is available without a prescription in many foreign markets, where it can be purchased over-the-counter (OTC) or "behind-the-counter" with pharmacist's assistance. For instance, in Australia it is an oral OTC product with a recommended adult dose of 0.3 or 0.6 mg, and a maximum daily dose of 1.2 mg [52]. Scopolamine can also be absorbed mucosally, as demonstrated by sublingual delivery [53, 54].

Scopolamine can also exhibit an antidepressant effect when administered intramuscularly [55], intravenously [56-58] (also disclosed in PCT International Publication No. WO 2006/127418), or orally [59]. Thus, scopolamine can affect at least one mood disorder (i.e., depression), which coincidentally is a co-morbid condition in many persons affected by panic disorder. Another muscarinic receptor antagonist, orphenadrine and its major metabolite, tofenacine, have also been reported to exhibit an antidepressant effect [60-62]. Although depression per se is not the intended medical indication of the present invention, selected antimuscarinic agents can display psychic (CNS) pharmacologic effect(s), such as the treatment and/or prophylaxis of depression (e.g., major depressive disorder, MDD).

Although not common knowledge among physicians at present, there is some historic evidence that scopolamine can exert anxiolytic effect(s). Scopolamine was described a century ago to have a "calming effect" (verbatim) when injected hypodermically into patients afflicted by various psychiatric disorders at doses of 0.2-1.0 mg, which are still relevant human doses to this day [63]. This 1906 publication mentioned, " . . . the calming effect of the medicament . . . The action of scopolamine shows itself rapid in maniacal excitement and in acute hallucinatory delirium. The patients become calm gradually, and fall asleep if the dose is somewhat larger."

A genetic study of the human M2 muscarinic receptor gene (CHRM2) has revealed an association between specific genetic polymorphisms and the risk of depression in major depressive syndrome [64]. Consistent with these pharmacologic and genetic findings in humans, laboratory studies with rodent models for antidepressant activity using both pharmacologic and gene knock-out approaches revealed that the antidepressant-like effects of scopolamine are mediated via the M1 and/or M2 receptors, but not the M3, M4, and M5 receptors [50]. Thus, the human M2 (and/or M1) receptor-linked second messenger signaling pathways in the CNS are likely to affect mood and mood disorders (e.g., depression).

Of relevance to our dual drug approach for acute anxiety and panic, a report disclosed the cardiovascular effects of oral atenolol (50 mg), oral scopolamine HBr (0.3 mg), coincident administration of both drugs, and no treatment in healthy volunteers when exposed to heat within a sauna [12]. Coincident administration of the two oral drugs revealed essentially the same cardiovascular effects as the beta blocker atenolol alone (i.e., reduced heart rate and blood pressure), and either at baseline prior to heat exposure or during it. A relevant antiemetic oral dose of scopolamine alone or as an adjunct to atenolol displayed essentially no effect with regard to the cardiovascular symptoms. Thus, the cardiovascular effects were due to atenolol. The potential for any psychiatric and/or psychic (CNS) effects of scopolamine were not envisioned or addressed by this study.

In view of these results [12] and given that acute anxiety and panic are driven physiologically in part by increased epinephrine's effects on the cardiovascular system, it is appropriate to include a beta blocker (e.g., atenolol) to address the cardiovascular symptoms per se. Scopolamine alone would not be anticipated to be of benefit for the cardiovascular symptoms of these psychiatric conditions. Palpitations resulting from elevated heart rate and/or blood pressure are considered the predominant symptom that patients are aware of during panic attacks and acute anxiety episodes. The beta blocker within the combinations of the present invention can address this primary (major) symptom.

The combination therapies of the present invention may also be of use in other psychiatric disorders, such as alcohol addiction and/or withdrawal, drug addiction and/or withdrawal, migraine, headache, and aggression.

The abuse of alcohol, prescription drugs, and illegal drugs (e.g., opioids/opiates and cocaine) are major mental health care concerns. The repetitive abuse of these chemicals can produce physiologic dependence, tolerance, and addiction. The symptoms of sudden withdrawal depend upon the abused substance, the impairment of neurological and neuroendocrine pathways, as well as visceral and peripheral somatic organ impairment. The withdrawal from addictive substances produces an array of acute symptoms, many of which overlap with the symptoms of panic and acute anxiety. Delirium tremens (DTs) occurs in some alcoholics upon abrupt cessation of drinking. The symptoms of alcohol-related DTs are very similar to those of panic attacks, and are in part related to beta adrenergic effects. The DTs can have serious and even life-threatening consequences. The standards-of-care for DTs are oral benzodiazepines. Withdrawal from opioid and/or opiate addiction is physiologically distinct from alcohol withdrawal.

With regard to beta blockers in substance abuse, atenolol has been shown in placebo-controlled trials to be beneficial in alcohol withdrawal [65-67]. Pindolol has been used to treat alcohol withdrawal [68]. Timolol had a minimal effect on a subset of symptoms of patients experiencing alcohol withdrawal [69]. With regard to beta blockers in cocaine abuse, propranolol has been used to treat withdrawal and overdoses [70, 71]. Note that propranolol has also been shown to suppress tremors [72], consistent with one of the perceived benefits of beta blockers in performance anxiety in musicians (above).

Alcohol dependence has been genetically linked to the human CHRM2 gene encoding the M2 muscarinic receptor (as also demonstrated for depression). Scopolamine has an M1 receptor preference over M2, but it can also bind the M2 receptor [50, 64]. Thus, there is a convergence between the genetic linkage and the pharmacologic studies, thereby providing a rationale for the use of scopolamine (or other muscarinic receptor antagonists) in treating alcohol addiction and/or withdrawal.

The prevalence of migraine in the USA according to the American Migraine Prevalence and Prevention (AMPP) study is 11.7% and probable migraine is 4.5%, for a combined total of 16.2% [73]. The rate is higher in females than in males. The dual drug approach of the present invention may be appropriate for the treatment of migraine and severe headache indications. Migraine is a co-morbid condition in approximately two-thirds of patients suffering from panic disorder [6, 74]. According to Smitherman and coworkers, "The first-line migraine prophylactics are not indicated for PD, and the selective serotonin re-uptake inhibitors used to treat PD are not efficacious for migraine; thus, separate agents are often required to address each condition." [6] Consistent with that comment, according to Marazziti and coworkers, " . . . the comorbidity of headache with panic disorder renders this condition more severe and possibly responsive to different treatments compared to panic disorder alone." [75] These two groups of authors are unaware of a single therapy that affects both migraine and PD. But, it is feasible that a combination of a beta blocker plus a muscarinic receptor antagonist may provide therapeutic benefit for both conditions—panic and migraine.

Beta-adrenergic receptor antagonists (e.g., atenolol, propranolol, metoprolol, nebivolol, nadolol) are considered to be effective prophylactics for chronic or episodic migraine [76-81]. Although one study reported no benefit from propranolol for treatment of acute symptoms [82], there is some, albeit limited, evidence that beta adrenergic receptor antagonists, especially when delivered mucosally, can also have benefit in the therapy of acute migraine [83, 84].

A patent by Innes (U.S. Pat. No. 4,532,244) suggests that transdermally-delivered scopolamine in a patch might be a prophylactic for migraine. However, the unconvincing evidence provided therein was based upon a single patient who used a scopolamine patch for 30 days. However, the biomedical literature is silent regarding whether scopolamine might be of benefit in preventing or treating migraine. Another muscarinic receptor antagonist, buclizine, is an API in an OTC combination drug (MIGRALEVE®) sold in the United Kingdom for the treatment of migraine.

The dual drug combination of the present invention may be therapeutic for migraine or headache, and especially so when delivered rapidly, for instance mucosally (e.g., sublingually).

In an embodiment, the dual drug approach of the present invention may be effective as a treatment for aggression. Systemic adrenaline can produce excited, anxious, and aggressive behavior in some individuals. Propranolol has been shown to have a therapeutic effect with regard to aggressive behavior [85, 86]. Augmentation of a beta blocker with the "calming effect" of scopolamine or another antimuscarinic agent may provide an effective medication for reducing aggression. For instance, scopolamine has been shown to reduce aggressive behavior in nonhuman primates under certain environmental circumstances [87].

The pharmaceutical standard-of-care for PA, PD, anxiety, and anxiety-related disorders by psychiatrists (and some other physicians) involves oral daily maintenance medication, whereas the present invention involves administration "as needed" (p.r.n.), and preferably on an occasional basis.

The pharmaceutical standard-of-care for PA, PD, anxiety, and anxiety-related disorders by psychiatrists (and some other physicians) is intended essentially for the long-term prophylaxis of episodes, whereas the present invention is intended for the short-term treatment of symptoms of episodes as they occur or immediately prior to an anticipated episode.

The pharmaceutical standard-of-care for PA, PD, anxiety, and anxiety-related disorders by psychiatrists (and some other physicians) includes SSRIs and/or benzodiazepines, none of which is the focus of the present invention. The common SSRIs and/or benzodiazepines can exhibit unwanted side effects, not anticipated by the dual drug combinations of the present invention.

Although many psychiatrists (and some other physicians) are aware of off-label (i.e., not FDA-approved) use of beta blockers as prophylactics for performance anxiety (e.g., stage fright during musical performances), the pharmaceutical standard-of-care for PA, PD, anxiety, and anxiety-related disorders by these physicians does not routinely include the use of beta blockers. Beta adrenergic receptor antagonists can provide limited benefit, such as the suppression of tachycardia, palpitations, and increased blood pressure, which are symptoms of panic and acute anxiety. These beta adrenergic receptor antagonist medications are typically administered for the treatment of hypertension. Thus, even though many psychiatrists are familiar with the off-label use of beta blockers for performance anxiety, as stated by Zamorski and Albucher, "Beta blockers, once widely touted as effective antipanic medications, have proven disappointing as monotherapy in subsequent placebo-controlled trials." [9]

There is a need to augment the limited benefits of a beta blocker (i.e., cardiovascular properties) with another type of active ingredient to produce a superior anti-panic or anti-anxiety therapy for use p.r.n. Furthermore, it would be advantageous for the other agent (i.e., non-beta blocker) to exert some psychic (CNS) pharmacologic benefit(s).

The pharmaceutical standard-of-care for PA, PD, anxiety, and anxiety-related disorders by psychiatrists (and some other physicians) does not include scopolamine. Prescription or over-the-counter (OTC) antiemetic medications acting as muscarinic receptor antagonists can suppress nausea, vomiting, sweating, motion sickness, sea sickness, morning sickness in pregnancy, some of which are symptoms of panic or acute anxiety. However, the transdermal patch of scopolamine does not provide suitable pharmacokinetics for rapid therapy of psychic or somatic symptoms that are the focus of the present invention [51]. Furthermore, some of the antiemetic APIs exhibit coincident antihistamine properties. Examples of the latter are diphenhydramine and meclizine.

Thus, in view of the foregoing, it follows that a pharmaceutical composition consisting essentially of a beta adrenergic receptor antagonist and a muscarinic receptor antagonist are not in use by psychiatrists, other physicians, or other prescribers (e.g., veterinarians or dentists) for treating PA, PD, anxiety, and anxiety-related disorders in particular, or any psychiatric condition for that matter in general. Outside of the present invention, we have found no evidence in the prior art of this particular type of dual drug combination therapy in use at present by psychiatrists, other physicians, or other prescribers for any therapeutic or prophylactic psychiatric indication(s) in humans or other mammals. Also, outside of the present invention, we have found no evidence in the prior art of a psychiatric therapy consisting essentially of a beta blocker and a muscarinic receptor antagonist agent together within a single pharmaceutical composition, or alternatively of coincident simultaneous administration of a pair of compositions, wherein one composition contains the beta blocker and the other contains the muscarinic receptor antagonist agent. Furthermore, these conclusions occur even though both classes of APIs (beta blockers and antimuscarinics) have been in commercial use for over five decades.

Furthermore, the pharmaceutical standard-of-care for PA, PD, anxiety, or anxiety-related disorders by psychiatrists and other physicians does not typically involve administration via a mucosal route, whereas the pharmaceutical compositions of the present invention may be delivered by this route, in addition to the oral route. The mucosal routes are especially useful and may be preferred in cases when "time is of the essence" in producing a pharmacologic effect and/or when the patient is unwilling or unable to swallow an oral solid or liquid dose form, or to be injected a parenteral dose form. Thus, mucosal delivery is an additional distinct benefit to the dual drug compositions of the present invention.

A dual drug combination is a well-known regulatory paradigm in the USA. There are ample predicate FDA-approved prescription drugs that contain two or more APIs. A common example is PERCOCET®, a combination of oxycodone and acetaminophen. Two additional recently-approved examples are NUDEXTA®, a combination of dextromethorphan and guinidine, and HARVONI®, a combination of ledipasvir and sofosbuvir. In addition, FDA-approved OTC drugs frequently contain more than one API.

Prior to the present invention there was a need for fast-acting (e.g., mucosally-delivered) pharmaceutical compositions for immediate p.r.n. treatment of acute symptoms of panic and acute anxiety. The present invention provides suitable solutions for this previously unmet medical need, and with the additional benefits of the APIs not being addictive and/or Controlled Substances.

BRIEF SUMMARY OF THE INVENTION

What we therefore believe to be comprised by our invention may be summarized inter alia in the following words.

A method for treating a psychiatric condition or disorder or the symptoms thereof, comprising administering to a living animal, including a human, a pharmaceutical composition consisting essentially of a therapeutically effective amount of a combination of at least one beta adrenergic receptor antagonist agent and/or pharmaceutically acceptable salts thereof, and at least one antiemetic muscarinic receptor antagonist agent and/or pharmaceutically acceptable salts thereof, such a method wherein the psychiatric condition or disorders are selected from the group consisting of panic attack, panic disorder, agoraphobia, anxiety, generalized anxiety disorder, social anxiety disorder, performance anxiety, alcohol addiction, alcohol withdrawal, drug addiction, drug withdrawal, migraine, headache, post-traumatic stress, post-traumatic stress disorder, and aggression, such a method wherein the symptoms of the psychiatric condition or disorder are selected from the group consisting of tachycardia, increased blood pressure, palpitations, nausea, vomiting, mental anxiety, fear, avoidance, dyspnea, hyperventilation, migraine, headache, sweating, trembling, post-traumatic stress, alcohol dependence, drug dependence, restlessness, irritability, and aggression, such a method wherein the at least one beta adrenergic receptor antagonist agent is selected from the group consisting of propranolol, atenolol, *Eucommia* extract, and/or pharmaceutically acceptable salts thereof, and wherein the at least one antiemetic muscarinic receptor antagonist agent is selected from the group consisting of scopolamine, diphenhydramine, meclizine, and/or pharmaceutically acceptable salts thereof, such a method wherein the at least one beta adrenergic receptor antagonist agent is propranolol or atenolol, and/or pharmaceutically acceptable salts thereof, in an amount of about 10 to 100 mg/dose for an adult, and wherein the at least one antiemetic muscarinic receptor antagonist agent is scopolamine, and/or pharmaceutically acceptable salts thereof, in an amount of about 0.05 to 1.0 mg/dose for an adult, and wherein the doses are lower for an adolescent or child, such a method wherein the pharmaceutical composition, when in liquid or semi-solid form, comprises at least one penetration-enhancing solvent selected from the group consisting of ethanol, glycerol, propylene glycol, ethoxydiglycol, and dimethylsulfoxide or, when in solid form, comprises at least one additional component selected from the group consisting of mannitol, a monosaccharide, a disaccharide, a bicarbonate buffer, a phosphate buffer, a binding agent, and a preservative, such a method wherein the pharmaceutical composition is in a form selected from the group consisting of a spray, an elixir, a solution, a suspension, an emulsion, a gel, a cream, a gum, a powder, a tablet, a capsule, a troche, a suppository, a pill, and a film, and wherein the pharmaceutical composition is administered to the animal, including a human, by a route of delivery selected from the group consisting of mucosal, sublingual, buccal, rectal, vaginal, nasal, parenteral, oral, and topical routes, such a method wherein the at least one beta adrenergic receptor antagonist agent is propranolol, atenolol, pindolol, nadolol, or nebivolol and/or pharmaceutically acceptable salts thereof, in an amount of about 10 to 100 mg/dose for an adult, and wherein the at least one antiemetic muscarinic receptor antagonist agent is scopolamine, and/or pharmaceutically acceptable salts thereof, in an amount of about 0.05 to 1.0 mg/dose for an adult, and wherein the doses are lower for an adolescent or child, and wherein the pharmaceutical composition is administered to the patient by a route of delivery selected from the group consisting of mucosal, sublingual, buccal, rectal, vaginal, nasal, parenteral, and oral routes, such a method wherein the pharmaceutical composition is administered pro re nata (p.r.n.) to the animal, including a human, by a route of delivery selected from the group consisting of mucosal, sublingual, buccal, rectal, vaginal, nasal, and parenteral routes for rapid therapeutic effect commencing within 30 minutes or less, or by the oral route of delivery, such a method wherein the at least one beta adrenergic receptor antagonist agent exerts therapeutic effects on somatic cardiovascular symptoms of the psychiatric condition or disorder, and the at least one antiemetic muscarinic receptor antagonist agent exerts therapeutic effects on somatic non-cardiovascular symptoms and/or central nervous system symptoms of the psychiatric condition or disorder, such a method wherein the pharmaceutical composition when administered to the living animal, including a human, exerts dryness of the mouth as a side effect of the muscarinic receptor antagonist agent, and wherein this side effect deters continuous or daily administration of the pharmaceutical composition in a human, such a method for treating a psychiatric condition or disorder or the symptoms thereof in a living animal, including a human, comprising administering to the patient anticipating symptoms of the psychiatric disorder and/or at the time of a trigger circumstance for the psychiatric disorder or condition, a pharmaceutical composition consisting essentially of at least one beta adrenergic receptor antagonist agent and/or pharmaceutically acceptable salts thereof, and at least one antiemetic muscarinic receptor antagonist agent and/or pharmaceutically acceptable salts thereof, in a therapeutically effective amount to stop or reduce the symptoms of the psychiatric disorder or condition, together with one or more pharmaceutically acceptable excipients, such a method wherein the at least one beta adrenergic receptor antagonist agent is selected from the group consisting of propranolol, atenolol, *Eucommia* extract, and/or pharmaceutically acceptable salts thereof, and wherein the at least one antiemetic muscarinic receptor antagonist agent is selected from the group consisting of scopolamine, diphenhydramine, meclizine, and/or pharmaceutically acceptable salts thereof, such a method wherein the at least one beta adrenergic receptor antagonist agent is selected from the group consisting of propranolol, atenolol, pindolol, nadolol, nebivolol, and/or pharmaceutically acceptable salts thereof and wherein the at least one antiemetic muscarinic receptor antagonist agent is scopolamine and/or pharmaceutically acceptable salts thereof, such a method wherein the at least one beta adrenergic receptor antagonist agent is propranolol or atenolol, and/or pharmaceutically acceptable salts thereof, in an amount of about 10 to 100 mg/dose for an adult, and wherein the at least one antiemetic muscarinic receptor antagonist agent is scopolamine, and/or pharmaceutically acceptable salts thereof, in an amount of about 0.05 to 1.0 mg/dose for an adult, and wherein the doses are lower for an adolescent or child, such a method wherein the pharmaceutical composition is administered pro re nata (p.r.n.) to the living animal, including a human, by a route of delivery selected from the group consisting of mucosal, sublingual, buccal, rectal, vaginal, nasal, and parenteral routes for rapid therapeutic effect commencing within 30 minutes or less, or by the oral route of delivery, such a method for treating a psychiatric disorder or condition or the symptoms thereof in a living animal, including a human, comprising concomitantly administering to the patient anticipating symptoms of the psychiatric disorder and/or at the time of a trigger event for symptoms of the psychiatric disorder or condition, a pharmaceutical composition consisting essentially of at least one beta adrenergic receptor antagonist agent and/or pharmaceutically acceptable salts thereof, and a pharmaceutical composition consisting essentially of at least one antiemetic muscarinic receptor antagonist agent and/or pharmaceutically acceptable salts thereof, in therapeutically effective amounts to stop or reduce the symptoms of the psychiatric disorder, such a method wherein the at least one beta adrenergic receptor antagonist agent is selected from the group consisting of propranolol, atenolol, *Eucommia* extract, and/or pharmaceutically acceptable salts thereof and wherein the at least one antiemetic muscarinic receptor antagonist agent is selected from the group consisting of scopolamine, diphenhydramine, meclizine, and/or pharmaceutically acceptable salts thereof, such a method wherein the at least one beta adrenergic receptor antagonist agent is selected from the group consisting of propranolol, atenolol, pindolol, nadolol, nebivolol, and/or pharmaceutically acceptable salts thereof and wherein the at least one antiemetic muscarinic receptor antagonist agent is scopolamine and/or pharmaceutically acceptable salts thereof, such a method wherein the at least one beta adrenergic receptor antagonist agent is propranolol or atenolol, and/or pharmaceutically acceptable salts thereof, in an amount of about 10 to 100 mg/dose for an adult, and wherein the at least one antiemetic muscarinic receptor antagonist agent is scopolamine, and/or pharmaceutically acceptable salts thereof, in an amount of about 0.05 to 1.0 mg/dose for an adult, and wherein the doses are lower for an adolescent or child, such a pharmaceutical composition consisting essentially of a combination of at least one beta adrenergic receptor antagonist agent and/or pharmaceutically acceptable salts thereof, and at least one antiemetic muscarinic receptor antagonist agent and/or pharmaceutically acceptable salts thereof, together with one or more pharmaceutically acceptable excipients and, when in a liquid or semi-solid form, comprises at least one penetration-enhancing solvent selected from the group consisting of ethanol, glycerol, propylene glycol, ethoxydiglycol, and dimethylsulfoxide, or when in a solid form comprises at least one additional component selected from the group consisting of mannitol, a monosaccharide, a disaccharide, a bicarbonate buffer, a phosphate buffer, a binding agent, and a preservative, such a pharmaceutical composition, wherein the at least one beta adrenergic receptor antagonist agent is selected from the group consisting of propranolol, atenolol, alprenolol, acebutolol, betaxolol, bisoprolol, bucindolol, celiprolol, nadolol, sotalol, esmolol, carteolol, carvedilol, mepindolol, nebivolol, oxprenolol, penbutolol, pindolol, landiolol, metoprolol, timolol, labetolol, *Eucommia* extract, and/or pharmaceutically acceptable salts thereof, such a pharmaceutical composition, wherein the at least one antiemetic muscarinic receptor antagonist agent is selected from the group consisting of scopolamine, diphenhydramine, meclizine, buclizine, cyclizine, hydroxyzine, pirenzepine, benztropine (benzatropine), atropine, hyoscyamine, butylscopolamine, methylscopolamine, doxylamine, promethazine, trihexyphenidyl, orphenadrine, and/or pharmaceutically acceptable salts thereof, such a pharmaceutical composition, wherein the at least one beta adrenergic receptor antagonist agent is selected from the group consisting of propranolol, atenolol, *Eucommia* extract, and/or pharmaceutically acceptable salts thereof and wherein the at least one antiemetic muscarinic receptor antagonist agent is selected from the group consisting of scopolamine, diphenhydramine, meclizine, and/or pharmaceutically acceptable salts thereof, such a pharmaceutical composition, wherein the at least one beta adrenergic receptor antagonist agent is selected from the group consisting of propranolol, atenolol, pindolol, nadolol, nebivolol, and/or pharmaceutically acceptable salts thereof and the at least one antiemetic muscarinic receptor antagonist agent is scopolamine and/or pharmaceutically acceptable salts thereof, such a pharmaceutical composition which is in a form selected from the group consisting of a spray, an elixir, a solution, a suspension, an emulsion, a gel, a cream, a gum, a powder, a tablet, a capsule, a troche, a suppository, a pill, and a film.

DETAILED DESCRIPTION OF THE INVENTION

In spite of the availability of many oral psychiatric pharmaceuticals (e.g., SSRIs and benzodiazepines), there is an unmet need for a fast-acting therapy for the p.r.n. treatment of symptoms of episodes of panic and acute anxiety. The present invention is focused primarily toward p.r.n. treatments of the symptoms of panic and anxiety, and preferably with rapid benefits. In an embodiment, the same or similar treatments may also have benefit with regard to selected other psychiatric disorders, such as alcohol addiction and/or withdrawal, drug addiction and/or withdrawal, migraine, headache, and aggression. The present invention addresses multiple aspects of this unmet medical need via the following beneficial features, among others.

Affecting Multiple Molecular Targets: The API combinations of the invention (e.g., propranolol and scopolamine) provide complementary pharmacologic benefits by interaction of the APIs with two or more dissimilar molecular targets. The biochemical pathways of the beta adrenergic and muscarinic receptor gene families are appropriate targets, as they are involved in some of the symptoms of PA, PD, generalized anxiety disorder, social anxiety disorder, and PTSD. Those molecular targets can be components of the central nervous system (CNS), the peripheral nervous system, and/or of somatic tissues (e.g., cardiovascular and gastrointestinal tissues). The appropriate combination of APIs affects more molecular targets than could be achieved by using a single API alone (e.g., an oral benzodiazepine). An antagonist of one class of receptors (e.g., muscarinic) can suppress one or more symptoms of PA. Whereas, an antagonist of the other class of receptors (e.g., beta adrenergic) can suppress other symptoms of PA. This could produce additive and/or synergistic effects of direct benefit to a patient afflicted by PA or anxiety. The invention is conceived to suppress multiple symptoms of panic and anxiety that are under the regulation of dissimilar biochemical pathways.

Stopping Symptoms or Reducing the Severity of Symptoms: The present invention stops or reduces (i.e., minimize the number or severity of) symptoms associated with panic- and anxiety-related disorders, such as tachycardia, increased blood pressure (especially systolic), palpitations, nausea, vomiting, mental anxiety, fear, avoidance, trembling (tremors), aberrant breathing (dyspnea and hyperventilation), sweating, migraine, headache, post-traumatic stress, and aggression.

Adverse And Beneficial Side Effects: The APIs of the present invention have desirable historic performance characteristics in humans. For example, APIs can be selected that are non-addicting and/or either non-sedating or minimally sedating. Sedation and lethargy are often problems for many oral daily anxiolytic therapies. Beta blockers are non-addicting and non-sedating. The antimuscarinic APIs are non-addicting, and can be non-sedating or minimally sedating at antiemetic doses. Furthermore, both classes of these APIs have been demonstrated to be well tolerated with minimal side effects during at least five decades of human use. Dryness of the mouth is a side effect of antiemetic antimuscarinic agents, which provides a benefit. Dry mouth may discourage the daily or persistent use of the dual drug combination therapies, thus reducing any potential for abuse.

Ease of Use: Given the episodic nature of panic and acute anxiety, it is beneficial to have a suitable pharmaceutical composition of the present invention available to a patient known to have manifested panic or anxiety disorder symptoms in the past. The pharmaceutical formulation could be in a purse, a pocket, a home, a workplace, yet could be immediately available for use "as needed" (p.r.n.) on occasion. At the time a patient encountered or anticipated an episode (e.g., a "trigger" circumstance was likely to occur) the combination therapy of the present invention can be administered mucosally (or orally) to stop or reduce (i.e., minimize the number or severity of) the symptoms of panic or acute anxiety. The ease of use of these compositions may minimize hospitalization, as in the case of acute psychiatric manifestations and/or substance abuse.

Replacement or Reduction in Use of Daily Oral Anxiolytic Medications: The present invention can replace or reduce the need for daily maintenance oral anxiolytic medications (e.g., SSRIs or benzodiazepines) that are used as "prophylactic" drugs. In many cases the latter are used continuously for months, years, or decades. Replacement or reduction of daily oral anxiolytic medications with the episodic therapy of the present invention could reduce a patient's risk of addiction, dependence, sedation, lethargy, drug tolerance, and toxic exposure to the conventional psychiatric medications. Furthermore, replacement of a "Controlled Substance" (i.e., benzodiazepine) with effective and non-addicting APIs is advantageous.

Rapid Drug Delivery by the Mucosal Route: The mucosal route of delivery provides for rapid penetration through the mucosa, followed by uptake into the circulatory system, resulting in systemic bioavailability without first-pass hepatic metabolism. Rapid drug delivery is feasible for mucosal routes, such as the sublingual, buccal, nasal, vaginal, or rectal routes. The speed at which one would expect a therapeutic benefit by a mucosal route would be second only to the intravenous (parenteral) route of administration. Oral or transdermal delivery is expected to be slower than the mucosal route, by minutes if not hours. Thus, in general the relative rates of absorption and therapeutic effect would be: intravenous>mucosal>oral>transdermal. Of these options, mucosal delivery is "optimal" and preferred in "time is of the essence" therapy, because it is convenient to administer and does not involve the self-administration by injection with needles.

It is normative for psychiatrists (and some other physicians) to treat patients afflicted with PA, PD, anxiety, and anxiety-related disorders with daily oral psychiatric medications. The intention is "maintenance" prophylaxis to block or suppress the onset of panic or anxiety. By comparison, the present invention provides a new paradigm for pharmaceutical therapy to be prescribed by physicians for patients having panic or anxiety. This new concept is not a persistent daily oral medication to replace a patient's routine daily benzodiazepine and/or SSRI medication; it is fundamentally different. The present invention is an episodic therapy for the symptoms of panic or anxiety, per se, and is to be taken "as needed" at the discretion of the patient. The patient who suffers only occasionally a PA event shall take the pharmaceutical composition of the present invention only occasionally. For instance, if a patient experienced only one panic or heightened anxiety event per week, then the medication of the present invention would be appropriate only at that time of the event or immediately preceding it (in anticipation of an event). Thus, therapy would be self-administered by a patient on only one day that week.

Another way of describing this is the difference between "chronic" maintenance medication vs. "acute" p.r.n. therapy for the symptoms of an episode. In this descriptive context, the normal practice of psychiatry is oral benzodiazepines or SSRIs as "chronic" maintenance medications. However, the new paradigm is "acute" p.r.n. therapy of symptoms by use of the compositions of the present invention. Unlike the abundance of choices of prophylactic medicines, there are presently no "fast-acting" drugs for the p.r.n. treatment of the acute symptoms of a panic attack per se at the time of an event or in immediate anticipation of an event.

The present invention may affect the somatic (e.g., peripheral and visceral) symptoms as well as the psychic (CNS) symptoms of panic- and anxiety-related disorders. The pharmaceutical compositions of the present invention were designed in view of an optimal treatment of the aggregate symptoms of panic attacks. The combination therapies may also be of benefit to patients manifesting somatic and/or psychic symptoms of anxiety and anxiety disorders, such as generalized anxiety disorder, social anxiety disorder (social phobia), performance anxiety (e.g., stage fright), agoraphobia, post-traumatic stress and PTSD. Furthermore, the combination therapies may also be beneficial in treating alcohol addiction and/or withdrawal (alcohol withdrawal syndrome), drug addiction and/or withdrawal (e.g., opioids, opiates), migraine, headache, and aggression.

The pharmaceutical compositions of the present invention consist essentially of an antiemetic muscarinic receptor antagonist drug and a beta adrenergic receptor antagonist drug, wherein the antiemetic muscarinic receptor antagonist drug and/or beta adrenergic receptor antagonist drug may be in the form of a free base or a pharmaceutically acceptable salt thereof.

The phrase "pharmaceutically acceptable", as used in connection with compositions of the invention, refers to molecular entities and other ingredients of such compositions that are physiologically tolerable and do not typically produce untoward reactions when administered to a mammal (e.g., human). Preferably, as used herein, the term "pharmaceutically acceptable" means approved by a regulatory agency of the Federal or a state government or listed in the U.S. Pharmacopeia (USP), National Formulary (NF), or other generally recognized pharmacopeia for use in mammals, and more particularly in humans. APIs of the present invention may be in the form of pharmaceutically acceptable salts. "Pharmaceutically acceptable salts" refers to those salts which possess the biological effectiveness and properties of the parent compound and which are not biologically or otherwise undesirable.

The pharmaceutical compositions of the present invention consist essentially of a beta adrenergic receptor antagonist drug and an antiemetic muscarinic receptor antagonist drug. One of the combination therapies of interest within the present invention is a beta blocker (e.g., propranolol or atenolol) plus scopolamine. The combination of a beta blocker and an antimuscarinic agent has not been used clinically for panic or anxiety indications, or for that matter any psychiatric medical indication, outside of the present invention.

The pharmaceutical compositions of the present invention may include, specifically, propranolol or atenolol (or other beta blockers) in combination with scopolamine (or other muscarinic receptor antagonist agents), or the salts, prodrugs, or analogs, derivatives, or metabolites thereof.

With regard to the pharmaceutically acceptable salts, propranolol HCl has been delivered sublingually at 10 and 40 mg per dose in adults [13, 14]. Propranolol in INDERAL® is available in oral doses ranging from 10 to 80 mg per dose for the treatment of hypertension. Depending on the indication multiple doses per day are permitted. The present invention provides a target dose in the range of about 10-100 mg per dose of propranolol in adults. It may be preferable to use a target dose of about 20-80 mg per adult, which are conventional dosages for treating hypertension. It might be even more preferable to use a target dose of about 20-40 mg per adult, especially for mucosal delivery. The dose for adolescents and children would be less than an adult's dose.

Atenolol is available in oral doses ranging from 25 to 100 mg per dose for the treatment of hypertension. Depending on the indication multiple doses per day are permitted. The present invention provides a target dose in the range of about 10-100 mg per dose of atenolol in adults. It might be more preferable to use a target dose of about 20-80 mg per adult. It might be even more preferable to use a target dose of about 20-50 mg per adult, especially for mucosal delivery. The dose for adolescents and children would be less than an adult's dose.

The pharmaceutical composition of the present invention comprises a beta adrenergic receptor antagonist agent selected from the group consisting of propranolol, atenolol, alprenolol, acebutolol, betaxolol, bisoprolol, bucindolol, celiprolol, nadolol, sotalol, esmolol, carteolol, carvedilol, mepindolol, nebivolol, oxprenolol, penbutolol, pindolol, landiolol, metoprolol, timolol, labetolol, and *Eucommia* extract, wherein the beta adrenergic receptor antagonist agent may be in the form of a free base or a pharmaceutically acceptable salt thereof.

The pharmaceutical composition of the present invention comprises an antiemetic muscarinic receptor antagonist agent selected from the group consisting of scopolamine, diphenhydramine, meclizine, buclizine, cyclizine, hydroxyzine, pirenzepine, benztropine (benzatropine), atropine, hyoscyamine, butylscopolamine, methylscopolamine, doxylamine, promethazine, trihexyphenidyl, and orphenadrine (or its metabolite, tofenacine), wherein the antiemetic muscarinic receptor antagonist agent may be in the form of a free base or a pharmaceutically acceptable salt thereof.

With regard to the pharmaceutically acceptable salts, scopolamine HBr has been delivered sublingually at 0.15 mg/dose in adults [53], orally at 0.4-1.0 mg/dose in adults [54, 59], and transdermally (TRANSDERMSCOP®) at 1.5 mg/dose/3 days in adults for the treatment of motion sickness, sea sickness, nausea and vomiting. The present invention provides a target dose range of about 0.05-1.0 mg of scopolamine in adults. It might be preferable to use a target dose of 0.2-0.6 mg per adult for oral delivery, and 0.05-0.3 mg per adult for mucosal delivery. For comparison, in Australia scopolamine is an OTC oral product with a recommended adult dose of 0.3 or 0.6 mg, and a maximum daily dose of 1.2 mg [52]. The dose for adolescents and children would be less than an adult's dose.

Closely-related derivatives of scopolamine are alternative antimuscarinic APIs, such as butylscopolamine, methylscopolamine, atropine, hyoscyamine (the levo isomer of atropine), and benztropine (benzatropine). For instance, peripherally-acting butylscopolamine (scopolamine butylbromide) is used for the treatment of abdominal spasms. The butylbromide modification prevents the API from crossing the blood-brain barrier. However, direct pharmacologic action by the antiemetic upon the CNS is preferable, if not necessary, for the present invention in mediating psychic benefits. Thus, in an embodiment, central-acting lipophilic antimuscarinic agents (e.g., scopolamine) are preferred, especially with regard to psychic symptoms (e.g., fear, avoidance, and mental anxiety). In addition, one can envision a medicinal chemistry approach to develop novel structure-activity relationship (SAR) series of CNS-active compounds related to scopolamine or other muscarinic inhibitors, which could be beneficial APIs for compositions of the present invention.

In addition to the scopolamine family of APIs, other closely-related families of APIs exhibiting antimuscarinic activities are included in the present invention. In some cases the APIs also exhibit antihistamine properties. Examples of other antiemetic antimuscarinic agents include: (a) diphenhydramine (BENADRYL®), orphenadrine (an OTC in Canada) and its metabolite tofenacine, and doxylamine (UNISOM® or NYQUIL®), all based upon an ethanolamine moiety; and (b) meclizine (DRAMAMINE® Less Drowsy Formulation or BONINE®), buclizine, cyclizine, hydroxyzine (ATARAX®), and pirenzepine, all based upon a piperazine moiety. Hydroxyzine is sometimes prescribed for anxiety [88] and might be beneficial in treating panic disorder [89]. As stated above, CNS accessibility by the muscarinic receptor antagonist is preferable. Pirenzepine is M1 selective, but it lacks CNS effects, and is thus less likely to produce some of the advantageous properties of this class of antagonists. Furthermore, other types of antiemetic antimuscarinic agents are available, such as promethazine and trihexyphenidyl.

The pharmaceutical compositions of the present invention may comprise one or more excipients. Excipients which may be used include carriers, surface active agents (surfactants), thickening (viscosity) agents, emulsifying agents, binding agents, dispersion or suspension agents, buffering agents, penetration-enhancing agents, solubilizers, colorants, sweeteners, flavoring agents, coatings, disintegrating agents, lubricants, preservatives, isotonic agents, and combinations thereof. The selection and use of suitable excipients is taught in Gennaro, ed., Remington: The Science and Practice of Pharmacy, 20th Ed. (Lippincott Williams & Wilkins 2003), the disclosure of which is incorporated herein by reference.

The term "carrier" applied to pharmaceutical compositions of the invention refers to a diluent, excipient, or vehicle with which an active compound is administered. Such pharmaceutical carriers can be liquids, such as water, saline solutions, aqueous dextrose solutions, aqueous glycerol solutions, and lipids and oils, including those of petroleum, animal, vegetable or synthetic origin. Suitable pharmaceutical carriers are described in "Remington's Pharmaceutical Sciences" by E. W. Martin, $18^{th}$ Edition.

The pharmaceutical compositions of the present invention consisting essentially of beta adrenergic receptor antagonists and muscarinic receptor antagonists may be in the form of a solid, a semi-solid, or a liquid dose form. Examples include sprays, elixirs, solutions, suspensions, emulsions, gels, creams, gums, powders, tablets, capsules, troches, suppositories, pills, and films. A variety of mechanical devices may be used to dispense the formulations, for instance pump applicators, spray applicators, and compressible tube dispensers. The devices may deliver calibrated unit doses, for instance in the cases of liquid or semi-solid dosage forms.

The pharmaceutical compositions of the present invention, when intended for sublingual, buccal, and/or oral delivery, may benefit from taste-masking with natural and/or artificial flavors and/or sweeteners (e.g., mannitol, monosaccharides, and disaccharides). Mouth paresthesia (numbness) can occur with propranolol HCl as a perceived adverse effect [14]. Paresthesia and an undesirable taste were observed for sublingual dose forms containing propranolol during development of the present invention. However, neither property was observed for atenolol in sublingual dose forms, thus providing two distinct advantages for this particular beta blocker.

In addition, using methods known to those skilled in the art, analogs and derivatives of the APIs of the invention can be created which have improved therapeutic efficacy in controlling panic and anxiety, i.e., higher potency and/or selectivity at a specific targeted receptor type, either greater or lower ability to penetrate mammalian blood-brain barriers, fewer side effects, etc.

The term "analog" or "derivative" or "metabolite" is used herein in the conventional pharmaceutical sense, to refer to a molecule that structurally resembles a reference molecule, but has been modified in a targeted and controlled manner to replace one or more specific substituents of the reference molecule with an alternate substituent, thereby generating a molecule which is structurally similar to the reference molecule. Synthesis and screening of analogs (e.g., using structural and/or biochemical analysis), to identify slightly modified versions of a known compound which may have improved or biased traits (such as higher potency and/or selectivity at a specific targeted receptor type, greater ability to penetrate mammalian blood-brain barriers, fewer side effects, etc.) is a drug design approach that is well known in pharmaceutical chemistry.

The pharmaceutical compositions of the present invention may include biocompatible buffering agents, such as sodium bicarbonate (pKa 6.4), sodium phosphate buffer (mono- and di-basic admixtures; pKa 6.8), or citric acid. For instance, in the event of sublingual or buccal delivery buffering to approximate the pH of saliva (pH 6.2-7.4) might be advantageous. In certain instances the chemical stability of one or more of the APIs within the formulation might benefit from the inclusion of biocompatible buffering agents. In certain conditions the physical stability of the liquid and/or semi-solid formulations might benefit from the inclusion of biocompatible buffering agents. Bicarbonates and phosphates are considered as physiologic buffers in mammals and humans. In certain compositions it might be preferable to maintain an acidic pH or acidic-to-neutral pH to prevent decomposition of an API (e.g., propranolol).

The pharmaceutical compositions of the present invention may include chemical preservatives, in addition to ethanol and/or glycerol in liquid and semi-solid compositions. Ethanol and glycerol are known to exhibit antibacterial properties. Examples of commonly used preservatives include sodium benzoate, benzyl alcohol, methyl paraben, propyl paraben, and butyl paraben, among others.

The pharmaceutical compositions of the present invention, when in liquid or semi-solid forms, may include one or more penetration-enhancing solvents such as ethanol, glycerol, propylene glycol, and/or ethoxydiglycol. In some circumstances, dimethylsulfoxide (DMSO) may be included as a skin penetration enhancer. However, DMSO may yield an unpleasant garlic flavor, even when applied to sites remote from the oral cavity.

Compositions of the present invention can also be formulated for vaginal or rectal administration, such as suppositories, films, viscous gels, creams, or retention enemas (e.g., containing conventional suppository bases such as cocoa butter or other glycerides).

The compositions may, if desired, be presented in a pack or dispenser device which may contain one or more unit dosage forms containing the active ingredient(s). The pack may, for example, comprise metal or plastic foil, such as a blister pack. Compositions of the invention formulated in a compatible pharmaceutical carrier may also be prepared, placed in an appropriate container, and labeled for treatment of an indicated condition.

The pharmaceutical compositions of the present invention may include surfactants, such as phospholipids (e.g., lecithin) and sodium lauryl sulfate. Surfactants help solubilize otherwise insoluble APIs or ingredients. Surfactants might be needed in certain drug combination compositions to produce emulsions or suspensions.

The pharmaceutical compositions of the present invention may include hydrophobic components, such as lipids, oils (e.g., isopropyl myristate and isopropyl palmitate), fatty acids, unsaturated fatty acids, waxes, petrolatum, lanolin, etc.

The pharmaceutical compositions of the present invention may include manufactured admixture "bases" typically used in extemporaneous compounding of pharmaceutical products. These "bases" are commercially available to pharmacists working in compounding pharmacies. Vendors of admixture "bases" include PCCA, Medisca, Letco, Paddock Laboratories, and Transderma, among others. In this context, the term "base" does not refer to alkalinity or pH. Rather they are "bases" into which active and/or inactive ingredients are mixed. The "bases" can be intended for specific routes of delivery, such as elixirs, syrups, and sweetened syrups for oral and oral mucosal delivery.

For administration in liquid or semi-solid forms, the APIs can be combined with pharmaceutically acceptable carriers (e.g., ethanol, glycerol, water), suspending agents (e.g., sorbitol syrup), emulsifying agents (e.g., lecithin), viscosity agents (e.g., methyl cellulose, polyethylene glycols, or Carbomer Homopolymer Type A), non-aqueous vehicles (e.g., a plant-derived oil), preservatives (e.g., a paraben), and the like. Stabilizing agents such as antioxidants (e.g., citric acid) can also be added.

For administration in the form of a tablet (sublingual or oral) or capsule (oral), the APIs can be combined with pharmaceutically acceptable excipients, such as binding agents (e.g., starch); fillers (e.g., mannitol); lubricants (e.g., magnesium stearate); dispersants or disintegrants (e.g., starch); or wetting agents (e.g., sodium lauryl sulphate), coloring and flavoring agents, gelatin, sweeteners (e.g., mono- or disaccharides), natural and synthetic gums (e.g., acacia), buffer salts (e.g., sodium bicarbonate), waxes, and the like.

The tablets can be coated by methods well known in the art. The compositions of the invention can be also introduced in microspheres, e.g., fabricated from polyglycolic acid/lactic acid (PGLA). Liquid preparations for oral administration can take the form of, for example, solutions, syrups, emulsions or suspensions, or they can be presented as a dry product (e.g., powder) for reconstitution with water or other suitable vehicle before use. Preparations for oral administration can be suitably formulated to give controlled or postponed release of the active compound. Controlled or postponed release may apply to one or more of the APIs within the composition, and may also apply to portions of one or more of the APIs within the composition. The APIs can also be administered in the form of liposome delivery systems. Liposomes can be formed from a variety of lipids and phospholipids, such as cholesterol, stearylamine or phosphatidylcholines, as is well known.

For administration by nasal inhalation, the therapeutics according to the present invention can be conveniently delivered in the form of an aerosol spray presentation from pressurized packs or a nebulizer, with the use of a suitable propellant, (e.g., dichlorodifluoromethane). In the case of a pressurized aerosol, the dosage unit can be determined by providing a valve to deliver a metered amount. Capsules (e.g., gelatin) and cartridges for use in an inhaler or insufflator can be formulated containing a powder mix of the compound and a suitable powder base such as lactose or starch.

The pharmaceutical compositions of the present invention may be delivered by mucosal or oral routes. A preferred route of delivery for the present invention is mucosal, as this route avoids GI metabolism and more significantly first-pass metabolism by the liver. For instance, within the oral mucosal environment at least two routes of absorption are possible—sublingual and buccal. Mucosal delivery is beneficial and preferred for p.r.n. administration, as well as to hasten the effects of the compositions. Coincidentally, a "chewing" gum (for sublingual, buccal, and/or oral delivery) might have the additional perceived benefit as a palliative agent. A patient could chew on it for some time while anticipating or waiting for the onset of a pharmacologic benefit.

Outside of the oral cavity, the pharmaceutical compositions of the present invention could be delivered to the mucosa of the rectum, the vagina, or nasal passages. These latter routes could be used in certain circumstances, such as a patient's aversion to the taste of a composition, or a patient's unwillingness or inability to swallow, or while a patient is prone to vomiting.

In addition to various mucosal routes of delivery (with expected rapid bioavailability), another preferred route is oral, essentially for ease-of-use by the patient. The oral route (e.g., tablets, capsules, and elixirs) is preferred when a patient anticipates in the future (e.g., in one hour) a "trigger" circumstance that is likely to lead into the onset of symptoms of panic or anxiety. The patient who expects to encounter a trigger circumstance self-administers the medication p.r.n. orally and waits a sufficient period of time (e.g., one hour) to enable GI absorption and bioavailability, prior to encountering the trigger. In other words, the effect of the oral route is likely to be somewhat delayed relative to a mucosal route.

In an embodiment, a topical formulation might be preferred, for instance to provide slower release or sustained-release of the combination of APIs. In another embodiment, in certain circumstances a parenteral formulation might be preferred, such as an intravenous injection intended for very rapid effect (e.g., less than 15 minutes) during symptoms of panic or anxiety.

The present invention is administered as a therapy to be taken at the time of an episode or in anticipation of an episode, rather than as a daily and/or persistent oral product for the prophylactic suppression of panic or anxiety. The pharmaceutical compositions of the invention are made available to the patient in advance of a panic or anxiety episode or a trigger circumstance thereof. The patient is able to self-medicate at the time of symptoms, or earlier at the time of the trigger, or even earlier in anticipation of the trigger. For instance, the p.r.n. self-administration of the dual drug combination might occur 10, 20, 30, 40, 50, or 60 minutes prior to the anticipated symptoms of panic or acute anxiety. Furthermore, when "time is of the essence" the mucosal routes of delivery are preferred, especially sublingual dose forms.

In an embodiment, a sublingual or buccal formulation is administered by the patient at the time of a panic or anxiety episode or in anticipation of a trigger of an episode, thus helping enable the patient to regain some or full control over their symptoms as needed.

In an embodiment, combination therapies with two (or more) APIs can be sold to patients in need of a treatment, albeit subject to various regulatory oversight processes. For instance within the USA, compounding pharmacies may formulate multiple APIs into a non-sterile compounded pharmaceutical product (via the 503A pathway) or into a sterile manufactured compounded pharmaceutical product (via the 503B pathway), provided that the APIs have been included in at least one FDA-approved medication. These compounded products are sold by prescription and are subject primarily to state boards of pharmacy. Alternatively, combination drug products may be approved for specific medical indications through the FDA's drug approval processes for sale to patients in need of therapy as either prescription drugs or over-the-counter (OTC) drugs. Thus, the combination therapies of the invention could be sold as "unapproved" compounded prescription (Rx) medicines, and/or as FDA-approved Rx drugs, and/or as FDA-approved OTC drugs.

The amount of APIs which can be combined with a carrier material to produce a single dosage form will vary depending upon the subject being treated, and the particular mode of administration, and will generally be that amount of the composition which produces a therapeutic effect. The dosage amount would be less in adolescents and children than in an adult, and might be a function of body mass or body surface area.

The present invention relates to compositions and methods for treating an animal, including a human. The subjects being treated with the present invention include adults, adolescents and children. The animals, including humans, may be patients under the care of a licensed physician, physician assistant, dentist, nurse practitioner, or veterinarian.

The present invention is useful in the p.r.n. treatment of non-human animals, such as under the care of a veterinarian. For instance, domesticated pets (e.g., dogs and cats) can be adversely affected by separation anxiety, as well as by specific phobic triggers, such as noises, containment, or treatment by a veterinarian or caretaker. Large domesticated livestock (e.g., cattle, swine, sheep, and horses) may also benefit from the anxiolytic compositions of the present invention. The dose ranges for the APIs required for therapeutically effective treatment of non-human animals can be estimated using allometric scaling from the intended human dose range.

The term "therapeutically effective" applied to dose or amount refers to that quantity of a compound or pharmaceutical composition that is sufficient to result in a desired activity upon administration to a living animal body.

A therapeutically effective amount of a pharmaceutical composition consisting essentially of a beta adrenergic receptor antagonist drug and an antiemetic muscarinic receptor antagonist drug, for example propranolol or atenolol and scopolamine, results in cessation or a decrease in severity of panic and anxiety symptoms, and/or a prevention or impairment of the onset of panic and anxiety symptoms.

In an embodiment, this invention provides pharmaceutical compositions consisting essentially of a beta adrenergic receptor antagonist drug and an antiemetic muscarinic receptor antagonist drug for self-administration by a patient experiencing anxiety, or in anticipation of panic or anxiety, and/or at the time of a trigger event for panic or anxiety, in order to stop or minimize the number or severity of the symptoms of panic or anxiety. The benefit of the dual drug approach is superior to an antimuscarinic therapy alone or a beta blocker therapy alone.

In an embodiment, this invention provides pharmaceutical compositions consisting essentially of propranolol or atenolol and scopolamine in a therapeutically effective amount to stop or reduce the symptoms of panic or anxiety.

Specific embodiments disclosed herein may be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In an embodiment, this invention provides a method for treating PA, PD, anxiety, or an anxiety disorder in a subject, comprising administering to a subject anticipating a PA or anxiety and/or at the time of a trigger circumstance for panic or anxiety, a pharmaceutical composition consisting essentially of propranolol or atenolol and scopolamine in a therapeutically effective amount to stop or reduce the symptoms of panic or anxiety.

In an embodiment, this invention provides a method for treating PA, PD, anxiety, or an anxiety disorder in a subject, comprising administering to a subject anticipating a PA or anxiety and/or at the time of a trigger circumstance for panic or anxiety, a pharmaceutical composition consisting essentially of a beta adrenergic receptor antagonist drug and an antiemetic muscarinic receptor antagonist drug in a therapeutically effective amount to stop or reduce the symptoms of panic or anxiety.

In a further embodiment, this invention provides a method for treating PA, PD, anxiety, or an anxiety disorder consisting of administering a pharmaceutical composition consisting essentially of a beta adrenergic receptor antagonist drug and an antiemetic muscarinic receptor antagonist drug in a therapeutically effective amount to stop or reduce the symptoms of anxiety or panic at the onset of anxiety or panic.

In yet another embodiment, this invention provides a method for treating anxiety, an anxiety-related disorder, PA, or PD in a subject, comprising concomitantly administering to the subject experiencing anxiety or panic, or anticipating anxiety or panic, and/or at the time of a trigger event for anxiety or panic, a pharmaceutical composition consisting essentially of a beta adrenergic receptor antagonist agent and a pharmaceutical composition consisting essentially of an antiemetic muscarinic receptor antagonist agent in therapeutically effective amounts to stop or reduce the symptoms of anxiety or panic.

In another embodiment, a broader group of psychiatric disorders extending beyond panic and anxiety may be treated p.r.n. using dual-drug compositions or two APIs in separate compositions concomitantly. The additional psychiatric disorders include alcohol addiction and/or withdrawal, drug addiction and/or withdrawal, migraine, headache, and aggression. Thus, in this broader context the symptoms of psychiatric disorders are selected from the group consisting of tachycardia, increased blood pressure, palpitations, nausea, vomiting, mental anxiety, fear, dyspnea, hyperventilation, migraine, headache, sweating, trembling (tremors), avoidance, post-traumatic stress, drug dependence, drug addiction, alcohol dependence, alcohol addiction, irritability, and aggression.

In yet another embodiment, a dual drug composition of the present invention provides a multiplicity of benefits to the patient afflicted by acute anxiety or panic. The beta blocker provides benefits with regard to cardiovascular symptoms (e.g., palpitations, heart rate, BP); the antimuscarinic agent provides benefits with regard to non-cardiovascular symptoms (e.g., nausea, vomiting, mental anxiety, avoidance, etc.); and the antimuscarinic agent provides another benefit as the result of it side effect, dry mouth. This latter side effect may help prevent abuse and addiction of the combination therapy intended for occasional p.r.n. usage. In other words, both the intended positive pharmacologic effects and the dry mouth side effect of the antimuscarinic agent is uniquely suited to a p.r.n. therapy approach, that is not appropriate or less appropriate for a daily oral anxiolytic medication.

EXAMPLES

The subject matter of the present invention will be better understood in connection with the following examples, which are intended as an illustration of and not a limitation upon the scope of the invention. It will be apparent to those skilled in the art that the described examples are merely representative in nature.

The active pharmaceutical ingredients of the present invention, together with one or more conventional adjuvants, carriers, or diluents, may be placed into the form of pharmaceutical compositions and unit dosages thereof, and in such form may be employed as solids (e.g., coated or uncoated tablets or filled capsules), or liquids or semi-solids (e.g., solutions, suspensions, emulsions, creams, gels, elixirs, or capsules filled with the same), all for oral or mucosal use; in the form of suppositories or capsules for rectal and vaginal administration.

Such pharmaceutical compositions and unit dosage forms thereof may comprise conventional or new ingredients in conventional or special proportions, with or without additional active compounds or principles, and such unit dosage forms may contain any suitable effective amount of the active ingredient commensurate with the intended dosage range to be employed. Tablets containing twenty (20) to two hundred (200) milligrams of active ingredient(s) or, more broadly, ten (10) to three hundred (300) milligrams of active ingredient(s) per tablet, are accordingly suitable representative unit dosage forms, as solids. With regard to liquids containing the combination therapeutic agents, such as alcoholic elixirs for oral or sublingual administration, a volume of about one hundred (100) microliters to about five (5) milliliters per unit dose is a suitable representative unit dosage volume. With regard to semi-solids containing the combination therapeutic agents, such as gels or creams for vaginal or rectal administration, a volume of about one half (0.5) milliliter to about five (5) milliliters is a suitable representative unit dosage volume. Consideration would also be given to the estimated maximum number of consecutive unit doses administered per period of time, such as per 6, 12, or 24 hours.

Example 1

Liquid Pharmaceutical Compositions

| Ingredients: | # 1 | # 2 | # 4 |
| --- | --- | --- | --- |
| Propranolol HCl | 1.2 g | 1.2 g | 1.2 g |
| Scopolamine HBr, Trihydrate | 15 mg | 30 mg | 15 mg |
| Ethanol, 95% | 1.5 ml | 3.0 ml | 3.0 ml |
| Glycerol | 1.5 ml | 3.0 ml | 3.0 ml |
| Propylene Glycol | 3.0 ml | 3.0 ml | — |
| Purified Water | QS 15 g | QS 15 g | QS 15 g |

As examples of aqueous liquid pharmaceutical compositions, alcoholic elixirs are prepared consisting of 80 mg/ml propranolol HCl, 1-2 mg/ml scopolamine HBr, 10-20% ethanol, 10-20% glycerol, and 0-20% propylene glycol. The dose is 0.5 ml of the alcoholic elixir in an adult, with a delivered dose of 40 mg propranolol HCl and 0.5 or 1.0 mg scopolamine HBr. The APIs are soluble in these elixirs at room temperature, but a precipitate may form at or near freezing when stored for multiple days in a refrigerator.

The preferred route of delivery for elixir compositions is oral. Taste-masking flavors and sweeteners may be incorporated into the composition, because propranolol HCl has an "acidic" and "medicine" taste and it produces mouth paresthesia when placed under or on the tongue. These undesirable properties were noted in humans during development of the liquid compositions. Alternative beta blockers may be chosen that lack these undesirable properties, such as atenolol.

The pH of the alcoholic elixirs (samples #1, 2, and 4) is ~4.5 without buffering. It may be beneficial to include a buffering agent or agents (e.g., bicarbonate or phosphate) to increase and buffer the pH to that of the oral cavity (~6.2-7.4) for sublingual or oral delivery. For instance, sodium bicarbonate can be included at a ratio (by mass) relative to propranolol HCl of about 1:50 to about 1:20, to increase the pH toward neutrality. For instance a ratio of ~1:26 of sodium bicarbonate to propranolol HCl raised the pH of elixir #4 to ~pH 6.5-7.0.

The alcohols (i.e., ethanol, glycerol, and propylene glycol) within the elixir may provide penetration enhancement of the APIs and a preservative property. The elixir can be dispensed by a unit-dose metered pump or spray applicator (e.g., delivering 0.5 or 0.25 ml for each pump action).

The alcoholic elixirs (samples #1, 2, and 4) had low viscosities of <10 cP when measured using a Brookfield viscometer.

In other liquid compositions, one may substitute other beta blockers in lieu of propranolol HCl and/or other antiemetic muscarinic receptor antagonist agents in lieu of scopolamine HBr.

Example 2

Viscous Liquids & Semi-Solid Pharmaceutical Compositions

| Ingredients: | # 7 | # 8 | # 9 | #10 |
|---|---|---|---|---|
| Propranolol HCl | 600 mg | 600 mg | 600 mg | 600 mg |
| Scopolamine HBr, Trihydrate | 15 mg | 15 mg | 15 mg | 15 mg |
| Glycerol | — | — | QS 15 g | QS 15 g |
| Propylene Glycol | 3.0 ml | 3.0 ml | 3.0 ml | 3.0 ml |
| Polyethylene Glycol (300) | — | 4.5 ml | 4.5 ml | 4.5 ml |
| Methyl Cellulose (4000 Mpas) | — | 300 mg | — | 300 mg |
| Spira-Wash Gel | QS 15 g | — | — | — |
| Sodium Bicarbonate | — | — | — | 30 mg |
| Purified Water | — | QS 15 g | — | — |

As examples of viscous liquid and semi-solid (e.g., gel, cream, or emulsion) pharmaceutical compositions for use in mucosal delivery (e.g., for rectal or vaginal application), formulations are prepared consisting of 40 mg/ml propranolol HCl and 1 mg/ml scopolamine HBr as the APIs. The inactive excipients are selected from: (a) alcoholic penetration enhancers and preservatives—propylene glycol and glycerol; (b) viscosity agents—polyethylene glycol, methyl cellulose, and Spira-Wash Gel™ base (PCCA); and (c) a buffering agent—sodium bicarbonate, for use in the rectum or in the vagina in post-menopausal women. Note that Spira-Wash Gel™ is an extemporaneous compounding base that contains polyethylene glycols and propylene glycol, among other ingredients. The dosage is 0.5 ml in an adult, with a delivered dose of 20 mg propranolol HCl and 0.5 mg scopolamine HBr.

The pH of the semi-solid formulations is ~4.5 without buffering (e.g., sample #8) and ~5.0-5.5 with bicarbonate buffering at a ratio of 1:20 of sodium bicarbonate to propranolol HCl (e.g., sample #10). The vagina of reproductive-age women is acidic (pH 3.8-4.4), and would not require a buffering agent. A buffering agent or agents (e.g., bicarbonate or phosphate) may be included to increase and buffer the pH toward the neutral pH of the rectum or post-menopausal vagina. A preservative agent may be included.

The viscosities of samples #9 and #10 were determined using a Brookfield viscometer at ca. 200-250 cP. The viscosities of samples #8-10 could be further increased by additional methylcellulose and/or higher molecular weight polyethylene glycol(s). Of the four samples, the most viscous is sample #7, containing Spira-Wash Gel (PCCA) as the majority component.

The aqueous semi-solids (or "viscous liquids") may be dispensed by a disposable single-dose applicator (e.g., delivers 0.5 or 1.0 ml for each pump action), such as a syringe-like device. Alternatively, semi-solid suppositories with higher viscosity may be prepared for manual insertion into the rectum or vagina.

In other viscous liquid or semi-solid compositions, one may substitute other beta blockers in lieu of propranolol HCl and/or other antiemetic muscarinic receptor antagonist agents in lieu of scopolamine HBr.

Example 3

Solid Pharmaceutical Compositions

| Ingredients: | # 11 | #13 | #14 | #23 | #25 |
|---|---|---|---|---|---|
| Propranolol HCl | 2.0 g | 2.0 g | — | — | — |
| Atenolol | — | — | 2.5 g | 1.83 g | 3.05 g |
| Scopolamine HBr, Trihydrate | 50 mg | 25 mg | 25 mg | 18 mg | 30 mg |
| Mannitol | 3.5 g | 3.34 g | 2.99 g | 2.86 g | 0.85 g |
| Starch | 1.4 g | 1.4 g | 1.4 g | 1.2 g | 1.0 g |
| Sodium Bicarbonate | 50 mg | 200 mg | 50 mg | 60 mg | 50 mg |
| Magnesium Stearate | — | 35 mg | 35 mg | 30 mg | 25 mg |
| Total | 7.0 g | 7.0 g | 7.0 g | 6.0 g | 5.0 g |

With regard to solid pharmaceutical compositions, powders, tablets, and capsules are prepared consisting of 10-80 mg propranolol HCl or 25-100 mg atenolol and 0.25-1.0 mg scopolamine HBr per dose. The inactive ingredients are selected from starch as the binding agent, mannitol as a sweetener, diluent, and dispersant, and sodium bicarbonate as a buffer and dispersant. Magnesium stearate may help in flow of the powder, especially in tablet-making using a mechanical tablet press. A preservative agent may be included in the formulation.

Tablets are formed by compression of the powder using a mechanical tablet press. For instance tablets without coatings are prepared with composition #11 at about 70 mg each, for use as sublingual or oral dose forms. At this size of tablet an adult dose would deliver 20 mg propranolol HCl and 0.5 mg scopolamine HBr. Alternatively, tablets may be produced using a triturate tablet mold (e.g., from the vendor PCCA), wherein the triturated powder is moistened with 95% ethanol and then the wells are filled with the moistened composition, extruded from the wells, and dried. The sublingual tablets dissolve rapidly under the tongue, for instance in less than one minute (e.g., solid dose forms #13 and 14). Propranolol HCl manifested an "acidic" and "medicine" taste as well as delayed paresthesia of the tongue in humans, whereas atenolol lacked these undesirable characteristics (i.e., comparison of solid dose forms #13 vs. 14). Sublingual (or buccal) tablets may be preferred for rapid disintegration, dissolution, absorption and increased bioavailability via the mucosal route. A sublingual tablet of #23 weighing ca. 82 mg delivers a dose of ca. 25 mg atenolol and ca. 0.25 mg of scopolamine HBr. Tablets may also be ingested orally, although it is rational to presume that absorption will be somewhat delayed and bioavailability will be somewhat reduced with many APIs, relative to the mucosal route.

As an alternative to tablets, gelatin capsules (or other biocompatible and biodegradable capsules) may be filled with the powder. Gelatin capsules may be selected to disintegrate or dissolve rapidly, for instance within 15 minutes or more preferably within 5 minutes in the stomach. Gelatin capsules would likely delay, albeit slightly, the absorption and pharmacologic effects, relative to a comparable uncoated tablet or liquid dose form. When "time is of the essence" for symptomatic treatment a gelatin capsule would not be preferred.

The preferred routes of delivery for solid compositions are oral and sublingual, although in certain circumstances tablets may be used in other mucosal routes of delivery. In an embodiment, taste-masking flavors and sweeteners other than mannitol, or in addition to mannitol, may be included in the formulation. Powders may be dispensed in pre-dosed quantities to be mixed into a drink (e.g., water) for ingestion. Powders intended for ingestion might not require starch or another binding agent. Tablets may be ingested orally or applied to the oral mucosal for sublingual (or buccal) delivery. Capsules (e.g., gel capsules) filled with the pharmaceutical composition may be ingested orally or opened to pour the powder into a drink.

A buffering agent or agents (e.g., bicarbonate or phosphate) may be included in formulations to increase and buffer the pH to that of the oral cavity (~6.2-7.4) for sublingual and/or buccal delivery. A buffering agent or agents might be included for oral medications (e.g., tablets or powders), although it should be noted that the stomach environment is acidic. Alkaline compositions could benefit from the use of an organic acid (e.g., citric acid) or buffer.

In other solid compositions, one may substitute other beta blockers in lieu of propranolol HCl or atenolol and/or other antiemetic muscarinic receptor antagonist agents in lieu of scopolamine HBr.

Example 4

Method of Treating

Due to their high degree of pharmacologic activity and their low toxicity, together presenting a most favorable therapeutic index, the active principles of the present invention are administered to a subject, e.g., a living animal (including a human) body, in need thereof, for the treatment, alleviation, amelioration, palliation, or elimination of a symptom or an indication or a condition which is susceptible thereto, or representatively of an indication or condition set forth elsewhere in this application, preferably concurrently, simultaneously, or together with one or more pharmaceutically-acceptable excipients, carriers, or diluents, especially and preferably in the form of a pharmaceutical composition thereof, whether by oral, sublingual, buccal, rectal, vaginal, transdermal, or parenteral route, in an effective amount. Suitable dosage ranges are 0.1-400 milligrams, preferably 0.1-200 milligrams, and especially 0.1-100 milligrams, depending as usual upon the historic dosages in humans for the individual APIs (albeit in combination) and the exact mode of administration, form in which administered, the indication toward which the administration is directed, the subject involved and the body weight or surface area of the subject involved, and the preference and experience of the physician or veterinarian in charge. The active agents of the present invention are administered orally, mucosally (e.g., buccally, by nasal inhalation, or rectally), topically, or parenterally in dosage unit formulations containing conventional non-toxic pharmaceutically acceptable carriers. It may be desirable to use the mucosal route to hasten the pharmacologic effects. Furthermore, it may be desirable to use the oral route.

As disclosed herein, the dose of the components in the compositions of the present invention is determined to ensure that the dose administered will not exceed an amount determined after consideration of either the historic dosing of the APIs in humans and the individual conditions of a patient, or the results obtained in test animals. A specific dose naturally varies depending on the dosage procedure, the conditions of a patient or a subject animal such as age, body weight, sex, sensitivity, feed, dosage period, drugs used in combination, seriousness of the disease. The appropriate dose and dosage times under certain conditions can be determined by the test based on the above-described indices but may be refined and ultimately decided according to the judgment of the practitioner and each patient's circumstances (age, general condition, severity of symptoms, sex, etc.) according to standard clinical techniques.

Toxicity and therapeutic efficacy of the APIs either alone or in compositions of the present invention can be determined by standard pharmaceutical procedures in experimental animals, e.g., by determining the $LD_{50}$ (the dose lethal to 50% of the population) and the $ED_{50}$ (the dose therapeutically effective in 50% of the population). The dose ratio between therapeutic and toxic effects is the therapeutic index and it can be expressed as the ratio $ED_{50}/LD_{50}$. APIs and/or compositions that exhibit large therapeutic indices are preferred.

Example 5

Mode of Treatment of Patients Affected by PA, PD, Anxiety, Anxiety-Related Disorders, and Other Psychiatric Disorders The present invention provides a self-administered p.r.n. symptomatic therapy taken by a patient in need thereof at the time of an episode of PA or anxiety, or in anticipation of a panic or anxiety episode, or at the time of a "trigger" circumstance for PA or anxiety. The pharmaceutical composition having an effective amount of a combination of an antimuscarinic drug and a beta adrenergic receptor antagonist drug is administered and temporarily alleviates some of the symptoms of PA, PD, agoraphobia, generalized anxiety disorder, social anxiety disorder/social phobia, performance anxiety, and/or PTSD at the time of a symptomatic episode or in anticipation of an episode.

Of the various anxiety-related disorders, it may be preferable to treat social anxiety disorder/social phobia and performance anxiety with the compositions of the present invention.

Compositions of the present invention may also be of value as a supportive p.r.n. therapy during cognitive behavioral therapy (CBT) or other forms of counseling for anxiety and panic patients. The compositions may provide anxiolytic benefit without cognitive impairment while learning or reinforcing desirable behaviors. The dual drug therapies may also be used when the patients experience acute anxiety episodes between sessions of CBT or other forms of counseling.

The symptoms which are alleviated by the combination therapy of an antimuscarinic drug and a beta adrenergic receptor antagonist drug include tachycardia, increased blood pressure, palpitations, nausea, vomiting, mental anxiety, fear, aberrant breathing (dyspnea and hyperventilation), sweating, trembling (tremors), migraine, headache, and post-traumatic stress. The present invention stops or diminishes the severity of one or more of these somatic and/or psychic symptoms. The present invention produces a calming effect in individuals, as discerned by the treated individual and/or observed by an objective observer.

The patients at the time of an episode of PA or anxiety or in anticipation of an episode of PA or anxiety may self-medicate by mucosal (e.g., sublingual, buccal, rectal, vaginal, or nasal) or oral routes, using the pharmaceutical compositions of the invention. Mucosal routes of drug delivery provide more rapid relief of symptoms compared to orally-ingested pharmaceutical compositions. Mucosal routes abrogate first-pass metabolism by the liver. Therefore, sublingual/buccal (or other mucosal) routes of administration provide immediate or more immediate relief when a patient has an episode of PA or anxiety, as well as in abrogating an episode of PA or anxiety upon encountering a trigger circumstance in advance of the expected symptoms.

The patients are treated p.r.n. sublingually or orally with solid dose compositions (e.g., tablets) consisting essentially of scopolamine at ~0.1-0.5 mg in combination with atenolol at ~25-50 mg or propranolol at ~20-40 mg, as representative examples. Other combinations of APIs and doses are also envisioned. Patients will experience beneficial abrogation or reduction in somatic and/or psychic symptoms of PA, PD, anxiety, or an anxiety disorder. The treatment provides an anxiolytic and/or calming effect. The beneficial effects (and side effects, if any) are hastened by the sublingual route of administration relative to an oral route of administration. As a specific example, a healthy adult subject administered sublingual atenolol plus scopolamine in tablet form, and at another time a sublingual propranolol plus scopolamine in tablet form. In each case a calming effect commenced in less than 15 minutes and lasted for multiple hours in duration, and without sedation. Dryness of the mouth was a side effect.

The dual drug approach is superior to treatments by the alternatives—most notably benzodiazepines (as well as opioids, opiates, or cannabinoids), especially given that the APIs of the present invention are non-addicting and not Controlled Substances that are often abused.

Patients affected by psychiatric disorders (beyond panic and acute anxiety) such as alcohol addiction and/or withdrawal, drug addiction and/or withdrawal, migraine, headache, and aggression are treated with similar dual-drug medications or two APIs in separate compositions concomitantly. In some instances these diverse psychiatric disorders are co-morbid with one another and/or share in common a set of symptoms. Upon administration, the dual-drug compositions affect a diversity of symptoms, such as tachycardia, increased blood pressure, palpitations, nausea, vomiting, mental anxiety, fear, dyspnea, hyperventilation, migraine, headache, sweating, trembling, avoidance, post-traumatic stress, drug dependence, alcohol dependence, restlessness, irritability, and aggression. The dual-drug approach, for instance scopolamine plus a beta blocker (e.g., atenolol or propranolol), affects most or all of the symptoms typically associated with PA, PD, anxiety, and anxiety disorders that are coincident with the other psychiatric conditions. Additional benefits may extend to other symptoms not typically associated with PA, PD, anxiety, or anxiety-related disorders. Furthermore, an anxiolytic or calming effect diminishes the number and magnitude of the symptoms experienced in the psychiatric disorders. Thus, somatic and psychic (CNS) symptoms will be affected by the dual-drug therapies of the present invention.

Example 6

Clinical Trials

Clinical trials are designed to study the combination therapies of the present invention. One type of trial design is termed as "in life" usage. The patients at the time of an episode of PA or anxiety, or in anticipation of an episode, or at the time of a "trigger" circumstance self-medicate by administering a pharmaceutical composition consisting essentially of an antimuscarinic drug and a beta adrenergic receptor antagonist drug and record by written or electronic means their specific symptoms of episodes, number and severity of symptoms of episodes, timing and frequency of use of the therapy (either at onset or in anticipation of), perceived benefits, perceived side-effects, etc. The patient's self-assessment(s) at specified time points can include analog (e.g., visual analog scale) or digital (e.g., binary or discrete unit scale) assessment tools.

This "in life" trial design mimics how the combination therapy is used in normal settings in a patient's life. The trials are "open label" in design, where the identity of the therapy is disclosed to the physicians and patients. Alternatively, a placebo of similar physical properties, yet lacking the APIs, is used as a control in "blinded" studies. In the latter case the patients can also undergo a cross-over trial design, in which the first period of time is on either the therapy or the placebo. Then, during the next period of time the patient is switched over to the alternative. The results are collected at later time points and analyzed by statistical methods to demonstrate efficacy and/or safety of the pharmaceutical compositions of the invention.

An alternative clinical trial design is the Trier Social Stress Test (TSST) to provoke anxiety. This method is used in a clinic and involves subjecting an individual to public speaking and mathematics questions as stressors. This approach has been used to study the effects of oral propranolol in volunteer subjects [25-28].

An alternative clinical trial design involves the intentional chemical provocation of a panic attack in a clinic. Several methods of provocation of PA have been reported, wherein a physician intentionally stimulates a physiologic response by: (a) sodium lactate infusion [90, 91]; (b) $CO_2$ inhalation [92]; and (c) cholecystokinin tetrapeptide (CCK-4) [90, 93]. These chemical exposures are used as tools to design controlled studies with predictable levels of PA episodes.

Patients afflicted by PA, PD, anxiety, or an anxiety disorder are enrolled in a provocation study (e.g., either TSST or chemical provocation). A placebo of similar physical properties, yet lacking the APIs, is used as a control in "blinded" studies. In the case of sublingual delivery (or other mucosal route) the drug or placebo is administered ~30 minutes prior to assessment, and in the case of oral delivery the drug or placebo is administered ~60 minutes prior to assessment. Alternatively, the trials are "open label" in design, where the identity of the therapy is disclosed to the physicians and/or patients. The clinical endpoints are selected from the following list: heart rate, palpitations, blood pressure (especially systolic), respiratory rate (dyspnea and hyperventilation), tremors, mental anxiety, fear, avoidance, nausea, migraine, headache, task performance, etc. The assessments of psychic anxiety can be assessed by the State-Trait Anxiety Inventory (STAI) or other similar tools [94, 95]. The results are collected in the clinic and analyzed by statistical methods to demonstrate efficacy and/or safety of the pharmaceutical compositions of the invention.

Clinical trials are designed for patients affected by other psychiatric disorders, beyond PA, PD, anxiety and anxiety disorders—such as alcohol addiction and/or withdrawal, drug addiction and/or withdrawal, migraine, headache, and aggression. The studies are conducted either "in life" (e.g., "open label" use of the compositions) or in a clinic setting. When desired, the trials may be placebo controlled and blinded to the investigators and/or patients. The preferred dosing is p.r.n., as the compositions are intended for occasional use in real life settings.

A patient affected by one or more of the psychiatric disorders self-administers either mucosally (e.g., sublingually) or orally a composition consisting essentially of scopolamine HBr (e.g., at preferably ca. 0.1-0.5 mg) in conjunction with a beta blocker (e.g., atenolol at preferably ca. 25-50 mg or propranolol HCl at preferably ca. 20-40 mg). Within an hour or less the patient and/or observer perceives benefit(s) with regard to symptoms. The therapeutic benefit(s) persist for multiple hours, for example, as long as 6 hours or even 24 hours. Following treatment the patient experiences an anxiolytic or calming effect that results in the perception of relief from anxiety, in addition to a reduction in cardiovascular symptoms (e.g., elevated heart rate, palpitations, and elevated blood pressure) due to epinephrine in the circulation. These benefits can be achieved at doses of the APIs that are non-sedating. The anxiolytic or calming effect can improve voluntary and involuntary motor control, task performance, cognition, memory, avoidance of harm or danger, and/or reduce fear in patients affected by the other psychiatric disorders. The benefit of the dual drug approach is superior to an antiemetic antimuscarinic therapy alone or a beta blocker therapy alone. Dryness of the mouth may occur as a side effect in some patients due to the antiemetic antimuscarinic agent (and especially so with sublingual delivery).

Example 7

Physicians' Prescriptions and Commercial Use

Prior to this present invention there were no commercial drug products available as combination therapies consisting essentially of a beta blocker plus an antiemetic antimuscarinic for the p.r.n. treatment of the symptoms of psychiatric disorders or conditions, or any medical condition for that matter. Therefore, an example of the utility and benefits of the present invention is physician prescriptions written by paper or electronic means for combination therapies for the treatment of the symptoms of PA, PD, anxiety, and anxiety disorders, and subject to the compositions and methods of the present invention.

Within the USA, it is anticipated that the combination therapies would typically require prescriptions under Federal and/or State laws, unless deemed as non-prescription OTC products. Physician prescriptions provide evidence of a physician's professional judgment as a licensed healthcare provider of the anticipated efficacy and safety of the combination therapies. The physician's prescription is also an evidence of a patient's desire and/or need for treatment, as applicable in individuals afflicted by the conditions of PA, PD, anxiety, and other psychiatric disorders. Furthermore, commercial sales of the prescription products of the combination therapies by a pharmacy are an additional evidence of the utility and benefits of the present invention.

Prescriptions and commercial sales of the pharmaceutical compositions of the present invention have recently commenced in the USA (albeit following the Priority Date of filing with the USPTO). Solid dose forms containing combinations of atenolol plus scopolamine, as well as propranolol plus scopolamine, have been prescribed by licensed medical professionals. Furthermore, the combination drug products have been delivered to the human patients, who were deemed by the licensed medical professionals to be in need of p.r.n. anxiolytic treatments by the oral and/or sublingual routes of administration. Thus, examples of the pharmaceutical compositions of the present invention have recently entered into commercial use in the USA.

Outside of the pharmaceutical compositions of the present invention, rapid-acting sublingual (or other mucosal) dose forms are not commercially available for either beta blockers or antimuscarinic agents. Beta blockers are readily available as oral solid dose forms. With regard to antimuscarinic agents, scopolamine is routinely prescribed as a topical patch in the USA, and multiple antiemetic antimuscarinic drugs are sold as oral (solid or liquid) dose forms. Thus, for the first time in commercial use the present invention has provided a dual drug combination approach to p.r.n. anxiolytic therapy, as well as non-oral routes of delivery.

Example 8

Patient Treatment

A patient diagnosed with and/or affected by PA, PD, anxiety, or an anxiety disorder is beginning to experience symptoms of a PA or acute anxiety (e.g., elevated heart rate, palpitations, or nausea) and self-administers p.r.n. a pharmaceutical composition consisting essentially of propranolol and scopolamine or atenolol and scopolamine. Some or all of the symptoms associated with a PA, PD, anxiety, or an anxiety disorder are suppressed and/or alleviated in the patient. The medication produces an anxiolytic and/or calming effect.

Example 9

Patient Treatment

A patient diagnosed with and/or affected by PA, PD, or anxiety is exposed to a trigger circumstance (e.g., flying, a crowd, or a noise) that has formerly resulted in a PA or anxiety and immediately self-administers p.r.n. a pharmaceutical composition consisting essentially of propranolol and scopolamine or atenolol and scopolamine. With or without treatment there may be a delay between encountering the trigger circumstance and the anticipated symptoms of PA or anxiety. As a result of treatment, some or all of the symptoms associated with PA or anxiety are prevented and/or alleviated in the patient. The medication produces an anxiolytic and/or calming effect.

Example 10

Patient Treatment

In certain panic- and acute anxiety-prone patients the pharmaceutical compositions of the invention consisting essentially of an antimuscarinic drug and a beta adrenergic receptor antagonist drug are sublingually or orally administered in advance of an anticipated trigger or symptoms of a PA or acute anxiety. When the patient anticipates a trigger or symptoms in 15-60 minutes in the future, then self-medication is started 15-60 minutes prior to the expected trigger or symptoms. Furthermore, when "time is of the essence" the mucosal route(s) of delivery are preferred (e.g., sublingual). For instance, if a patient desires the effect of the medication in 30 minutes or less, the mucosal route(s) of delivery are preferred, whereas if the patient desires the effect beyond 30 minutes then the oral route of delivery may be preferred. It follows that an oral gelatin capsule would delay somewhat the therapeutic benefits, and is not preferred for rapid therapy.

The efficacious benefit of a single administered dose will last for hours, provided sufficient blood levels of the antimuscarinic and/or the anti-beta adrenergic APIs are sustained. The overt effects of a single dose may diminish over the course of a day, as the APIs are progressively metabolized and/or excreted. Note that both scopolamine and propranolol are metabolized by the liver, whereas atenolol is not. Thus, an impairment of hepatic functions might prolong the effects of the certain drug combinations. The blood levels of the APIs are influenced by multiple pharmacologic and physiologic parameters, such as absorption, distribution, metabolism, and excretion (ADME), as well as other individual patient genetic and environmental conditions. It follows that the blood levels of the APIs are expected to vary somewhat from patient to patient. This variability could affect efficacy.

Example 11

Patient Treatment

Patients affected by psychiatric disorders beyond panic and anxiety, such as alcohol addiction and/or withdrawal, drug addiction and/or withdrawal, migraine, headache, and aggression are treated in a similar manner using the pharmaceutical compositions of the present invention. Following treatment the patient experiences an anxiolytic and/or calming effect that results in the perception of relief from anxiety, in addition to a reduction in cardiovascular symptoms (e.g., elevated heart rate, palpitations, and elevated blood pressure) due to epinephrine in the circulation. The anxiolytic or calming effect may improve cognition, memory, voluntary and involuntary motor control, task performance, avoidance of harm or danger, and/or may reduce fear in patients affected by the other psychiatric disorders. The dual-drug approach coincidentally reduces the number and/or severity of the symptoms associated with these disorders. The benefit of the dual drug approach is superior to an antimuscarinic therapy alone or a beta blocker therapy alone. The dual drug approach is superior to treatments by the alternatives—benzodiazepines, opioids, opiates, or cannabinoids, especially given that the APIs of the present invention are non-addicting and not Controlled Substances that are often abused. Dryness of the mouth may occur as a side effect in some patients.

The present invention is not to be limited in scope by the specific embodiments described herein. Indeed, various modifications of the invention in addition to those described herein will become apparent to those skilled in the art from the foregoing description.

All patents, applications, publications, test methods, literature, and other materials cited herein are hereby incorporated by reference.

REFERENCES

1. Kessler, R. C., et al., *The epidemiology of panic attacks, panic disorder, and agoraphobia in the National Comorbidity Survey Replication*. Arch Gen Psychiatry, 2006. 63(4): p. 415-24.
2. Kessler, R. C., et al., *Prevalence, severity, and comorbidity of 12-month DSM-IV disorders in the National Comorbidity Survey Replication*. Arch Gen Psychiatry, 2005. 62(6): p. 617-27.
3. Kessler, R. C., et al., *Lifetime prevalence and age-of-onset distributions of DSM-IV disorders in the National Comorbidity Survey Replication*. Arch Gen Psychiatry, 2005. 62(6): p. 593-602.
4. Wang, P. S., et al., *Twelve-month use of mental health services in the United States: results from the National Comorbidity Survey Replication*. Arch Gen Psychiatry, 2005. 62(6): p. 629-40.
5. Andrade, L., W. W. Eaton, and H. Chilcoat, *Lifetime comorbidity of panic attacks and major depression in a population-based study*. Symptom profiles. Br J Psychiatry, 1994. 165(3): p. 363-9.
6. Smitherman, T. A., E. D. Kolivas, and J. R. Bailey, *Panic disorder and migraine: comorbidity, mechanisms, and clinical implications*. Headache, 2013. 53(1): p. 23-45.
7. Breslau, N., et al., *Headache types and panic disorder: directionality and specificity*. Neurology, 2001. 56(3): p. 350-4.
8. Schneier, F. R., *Clinical practice. Social anxiety disorder*. N Engl J Med, 2006. 355(10): p. 1029-36.
9. Zamorski, M. A. and R. C. Albucher, *What to do when SSRIs fail: eight strategies for optimizing treatment of panic disorder*. Am Fam Physician, 2002. 66(8): p. 1477-84.
10. Altamura, A. C., et al., *Understanding the pharmacokinetics of anxiolytic drugs*. Expert Opin Drug Metab Toxicol, 2013. 9(4): p. 423-40.
11. Greenblatt, D. J., et al., *Pharmacokinetic comparison of sublingual lorazepam with intravenous, intramuscular, and oral lorazepam*. J Pharm Sci, 1982. 71(2): p. 248-52.
12. Kukkonen-Harjula, K., et al., *Cardiovascular effects of Atenolol, scopolamine and their combination on healthy men in Finnish sauna baths*. Eur J Appl Physiol Occup Physiol, 1994. 69(1): p. 10-5.
13. Wang, Y., et al., *Clinical pharmacokinetics of buffered propranolol sublingual tablet (Promptol)—application of a new "physiologically based" model to assess absorption and disposition*. AAPS J, 2013. 15(3): p. 787-96.
14. Mansur, A. P., et al., *Pharmacokinetics and pharmacodynamics of propranolol in hypertensive patients after sublingual administration: systemic availability*. Braz J Med Biol Res, 1998. 31(5): p. 691-6.
15. Duchateau, G. S., J. Zuidema, and F. W. Merkus, *Bioavailability of propranolol after oral, sublingual, and intranasal administration*. Pharm Res, 1986. 3(2): p. 108-11.
16. Morimoto, K., et al., *Design of polyvinyl alcohol hydrogel as a controlled-release vehicle for rectal administra-* tion of dl-propranolol-HCl and atenolol. Chem Pharm Bull (Tokyo), 1989. 37(9): p. 2491-5.
17. *Propranolol.* Br Med J, 1966. 2(5525): p. 1311-2.
18. Ravaris, C. L., et al., *A controlled study of alprazolam and propranolol in panic-disordered and agoraphobic outpatients.* J Clin Psychopharmacol, 1991. 11(6): p. 344-50.
19. Tyrer, P. J. and M. H. Lader, *Physiological response to propranolol and diazepam in chronic anxiety.* Br J Clin Pharmacol, 1974. 1(5): p. 387-90.
20. Tyrer, P. J. and M. H. Lader, *Response to propranolol and diazepam in somatic and psychic anxiety.* Br Med J, 1974. 2(5909): p. 14-6.
21. Becker, A. L., *Oxprenolol and propranolol in anxiety states. A double-blind comparative study.* S Afr Med J, 1976. 50(16): p. 627-9.
22. Munjack, D. J., et al., *Alprazolam, propranolol, and placebo in the treatment of panic disorder and agoraphobia with panic attacks.* J Clin Psychopharmacol, 1989. 9(1): p. 22-7.
23. Drew, P. J., J. N. Barnes, and S. J. Evans, *The effect of acute beta-adrenoceptor blockade on examination performance.* Br J Clin Pharmacol, 1985. 19(6): p. 783-6.
24. Faigel, H. C., *The effect of beta blockade on stress-induced cognitive dysfunction in adolescents.* Clin Pediatr (Phila), 1991. 30(7): p. 441-5.
25. Andrews, J. and J. C. Pruessner, *The combined propranolol/TSST paradigm—a new method for psychoneuroendocrinology.* PLoS One, 2013. 8(2): p. e57567.
26. Alexander, J. K., et al., *Beta-adrenergic modulation of cognitive flexibility during stress.* J Cogn Neurosci, 2007. 19(3): p. 468-78.
27. Kudielka, B. M., et al., *No effect of 5-day treatment with acetylsalicylic acid (aspirin) or the beta-blocker propranolol (Inderal) on free cortisol responses to acute psychosocial stress: a randomized double-blind, placebo-controlled study.* Neuropsychobiology, 2007. 56(2-3): p. 159-66.
28. von Kanel, R., et al., *Aspirin, but not propranolol, attenuates the acute stress-induced increase in circulating levels of interleukin-6: a randomized, double-blind, placebo-controlled study.* Brain Behav Immun, 2008. 22(2): p. 150-7.
29. Papadopoulos, A., et al., *The effects of single dose anxiolytic medication on the CO2 models of anxiety: differentiation of subjective and objective measures.* J Psychopharmacol, 2010. 24(5): p. 649-56.
30. Pitman, R. K., et al., *Pilot study of secondary prevention of posttraumatic stress disorder with propranolol.* Biol Psychiatry, 2002. 51(2): p. 189-92.
31. Vaiva, G., et al., *Immediate treatment with propranolol decreases posttraumatic stress disorder two months after trauma.* Biol Psychiatry, 2003. 54(9): p. 947-9.
32. Hoge, E. A., et al., *Effect of acute posttrauma propranolol on PTSD outcome and physiological responses during script-driven imagery.* CNS Neurosci Ther, 2012. 18(1): p. 21-7.
33. Bell, J., *Propranolol, post-traumatic stress disorder and narrative identity.* J Med Ethics, 2008. 34(11): p. e23.
34. Cahill, S. P., K. Pontoski, and C. M. D'Olio, *Posttraumatic Stress Disorder and Acute Stress Disorder II: Considerations for Treatment and Prevention.* Psychiatry (Edgmont), 2005. 2(9): p. 34-46.
35. Stein, M. B., et al., *Pharmacotherapy to prevent PTSD: Results from a randomized controlled proof-of-concept trial in physically injured patients.* J Trauma Stress, 2007. 20(6): p. 923-32.
36. McGhee, L. L., et al., *The effect of propranolol on posttraumatic stress disorder in burned service members.* J Burn Care Res, 2009. 30(1): p. 92-7.
37. Beversdorf, D. Q., et al., *Central beta-adrenergic modulation of cognitive flexibility.* Neuroreport, 2002. 13(18): p. 2505-7.
38. Silver, J. A., et al., *Effect of anxiolytics on cognitive flexibility in problem solving.* Cogn Behav Neural, 2004. 17(2): p. 93-7.
39. Neftel, K. A., et al., *Stage fright in musicians: a model illustrating the effect of beta blockers.* Psychosom Med, 1982. 44(5): p. 461-9.
40. Ellis, M. E., et al., *Cardioselectivity of atenolol in asthmatic patients.* Eur J Clin Pharmacol, 1981. 21(3): p. 173-6.
41. James, I. and I. Savage, *Beneficial effect of nadolol on anxiety-induced disturbances of performance in musicians: a comparison with diazepam and placebo.* Am Heart J, 1984. 108(4 Pt 2): p. 1150-5.
42. Gates, G. A., et al., *Effect of beta blockade on singing performance.* Ann Otol Rhinol Laryngol, 1985. 94(6 Pt 1): p. 570-4.
43. Hanania, N. A., et al., *The safety and effects of the beta-blocker, nadolol, in mild asthma: an open-label pilot study.* Pulm Pharmacol Ther, 2008. 21(1): p. 134-41.
44. James, I. M., W. Burgoyne, and I. T. Savage, *Effect of pindolol on stress-related disturbances of musical performance: preliminary communication.* J R Soc Med, 1983. 76(3): p. 194-6.
45. Pessina, A. C., *Metabolic effects and safety profile of nebivolol.* J Cardiovasc Pharmacol, 2001. 38 Suppl 3: p. S33-5.
46. Cheng, J. W., *Nebivolol: a third-generation beta-blocker for hypertension.* Clin Ther, 2009. 31(3): p. 447-62.
47. Navas, E. V. and D. O. Taylor, *Q: Can patients with COPD or asthma take a beta-blocker?* Cleve Clin J Med, 2010. 77(8): p. 498-9.
48. Greenway, F., et al., *A clinical trial testing the safety and efficacy of a standardized Eucommia ulmoides Oliver bark extract to treat hypertension.* Altern Med Rev, 2011. 16(4): p. 338-47.
49. Brantigan, C. O., T. A. Brantigan, and N. Joseph, *Effect of beta blockade and beta stimulation on stage fright.* Am J Med, 1982. 72(1): p. 88-94.
50. Witkin, J. M., et al., *M1 and m2 muscarinic receptor subtypes regulate antidepressant-like effects of the rapidly acting antidepressant scopolamine.* J Pharmacol Exp Ther, 2014. 351(2): p. 448-56.
51. Nachum, Z., A. Shupak, and C. R. Gordon, *Transdermal scopolamine for prevention of motion sickness: clinical pharmacokinetics and therapeutic applications.* Clin Pharmacokinet, 2006. 45(6): p. 543-66.
52. Corallo, C. E., A. Whitfield, and A. Wu, *Anticholinergic syndrome following an unintentional overdose of scopolamine.* Ther Clin Risk Manag, 2009. 5(5): p. 719-23.
53. Imai, K., et al., *Sublingually administered scopolamine for nausea in terminally ill cancer patients.* Support Care Cancer, 2013. 21(10): p. 2777-81.
54. Gray, M. Y., *The use of anticholinergics for the management of terminal secretions.* Evidence Matters (Hospice Pharmacia newsletter), 2007. 1(3): p. 1-6.
55. Gillin, J. C., et al., *The effects of scopolamine on sleep and mood in depressed patients with a history of alcoholism and a normal comparison group.* Biol Psychiatry, 1991. 30(2): p. 157-69.
56. Drevets, W. C. and M. L. Furey, *Replication of scopolamine's antidepressant efficacy in major depressive dis-* order: a randomized, placebo-controlled clinical trial. Biol Psychiatry, 2010. 67(5): p. 432-8.
57. Furey, M. L., et al., *Scopolamine produces larger antidepressant and antianxiety effects in women than in men.* Neuropsychopharmacology, 2010. 35(12): p. 2479-88.
58. Furey, M. L. and W. C. Drevets, *Antidepressant efficacy of the antimuscarinic drug scopolamine: a randomized, placebo-controlled clinical trial.* Arch Gen Psychiatry, 2006. 63(10): p. 1121-9.
59. Khajavi, D., et al., *Oral scopolamine augmentation in moderate to severe major depressive disorder: a randomized, double-blind, placebo-controlled study.* J Clin Psychiatry, 2012. 73(11): p. 1428-33.
60. Capstick, N. and H. Pudney, *A comparative trial of orphenadrine and tofenacin in the control of depression and extrapyramidal side-effects associated with fluphenazine decanoate therapy.* J Int Med Res, 1976. 4(6): p. 435-40.
61. Onuaguluchi, G., *Assessment of drug therapy in Parkinsonism.* Br Med J, 1963. 1(5328): p. 443-8.
62. Bram, G. and N. Shanmuganathan, *An evaluation of tofenacine (elamol), a new drug for the treatment of depression.* Curr Ther Res Clin Exp, 1971. 13(10): p. 625-30.
63. Houde, A., *Scopolamine: A Physiological and Clinical Study.* The American Journal of Clinical Medicine, 1906. 13: p. 365-367.
64. Wang, J. C., et al., *Evidence of common and specific genetic effects: association of the muscarinic acetylcholine receptor M2 (CHRM2) gene with alcohol dependence and major depressive syndrome.* Hum Mol Genet, 2004. 13(17): p. 1903-11.
65. Kraus, M. L., et al., *Randomized clinical trial of atenolol in patients with alcohol withdrawal.* N Engl J Med, 1985. 313(15): p. 905-9.
66. Horwitz, R. I., L. D. Gottlieb, and M. L. Kraus, *The efficacy of atenolol in the outpatient management of the alcohol withdrawal syndrome. Results of a randomized clinical trial.* Arch Intern Med, 1989. 149(5): p. 1089-93.
67. Gottlieb, L. D., et al., *Randomized controlled trial in alcohol relapse prevention: role of atenolol, alcohol craving, and treatment adherence.* J Subst Abuse Treat, 1994. 11(3): p. 253-8.
68. Digranes, O., *[Beta blocker treatment in alcohol withdrawal. A double-blind test with pindolol (Visken)/placebo].* Tidsskr Nor Laegeforen, 1976. 96(4): p. 226-8.
69. Potter, J. F., L. T. Bannan, and D. G. Beevers, *The effect of a non-selective lipophilic beta-blocker on the blood pressure and noradrenaline, vasopressin, cortisol and renin release during alcohol withdrawal.* Clin Exp Hypertens A, 1984. 6(6): p. 1147-60.
70. Kampman, K. M., et al., *Effectiveness of propranolol for cocaine dependence treatment may depend on cocaine withdrawal symptom severity.* Drug Alcohol Depend, 2001. 63(1): p. 69-78.
71. Kampman, K. M., et al., *A double-blind, placebo-controlled trial of amantadine, propranolol, and their combination for the treatment of cocaine dependence in patients with severe cocaine withdrawal symptoms.* Drug Alcohol Depend, 2006. 85(2): p. 129-37.
72. Koller, W. C. and N. Biary, *Effect of alcohol on tremors: comparison with propranolol.* Neurology, 1984. 34(2): p. 221-2.
73. Smitherman, T. A., et al., *The prevalence, impact, and treatment of migraine and severe headaches in the United States: a review of statistics from national surveillance studies.* Headache, 2013. 53(3): p. 427-36.
74. Yamada, K., et al., *High prevalence of comorbidity of migraine in outpatients with panic disorder and effectiveness of psychopharmacotherapy for both disorders: a retrospective open label study.* Psychiatry Res, 2011. 185(1-2): p. 145-8.
75. Marazziti, D., et al., *Prevalence of headache syndromes in panic disorder.* Int Clin Psychopharmacol, 1999. 14(4): p. 247-51.
76. Loder, E., R. Burch, and P. Rizzoli, *The 2012 AHS/AAN guidelines for prevention of episodic migraine: a summary and comparison with other recent clinical practice guidelines.* Headache, 2012. 52(6): p. 930-45.
77. Shamliyan, T. A., et al., *Episodic migraines in children: limited evidence on preventive pharmacological treatments.* J Child Neurol, 2013. 28(10): p. 1320-41.
78. Schellenberg, R., et al., *Nebivolol and metoprolol for treating migraine: an advance on beta-blocker treatment?* Headache, 2008. 48(1): p. 118-25.
79. Holroyd, K. A., et al., *Effect of preventive (beta blocker) treatment, behavioural migraine management, or their combination on outcomes of optimised acute treatment in frequent migraine: randomised controlled trial.* BMJ, 2010. 341: p. c4871.
80. Diamond, S., *Strategies for migraine management.* Cleve Clin J Med, 1991. 58(3): p. 257-61.
81. Edvardsson, B., *Atenolol in the prophylaxis of chronic migraine: a 3-month open-label study.* Springerplus, 2013. 2: p. 479.
82. Banerjee, M. and L. Findley, *Propranolol in the treatment of acute migraine attacks.* Cephalalgia, 1991. 11(4): p. 193-6.
83. Migliazzo, C. V. and J. C. Hagan, 3rd, *Beta blocker eye drops for treatment of acute migraine.* Mo Med, 2014. 111(4): p. 283-8.
84. Chiam, P. J., *Topical beta-blocker treatment for migraine.* Int Ophthalmol, 2012. 32(1): p. 85-8.
85. Silver, J. M., et al., *Propranolol treatment of chronically hospitalized aggressive patients.* J Neuropsychiatry Clin Neurosci, 1999. 11(3): p. 328-35.
86. Lader, M., *Beta-adrenoceptor antagonists in neuropsychiatry: an update.* J Clin Psychiatry, 1988. 49(6): p. 213-23.
87. Plotnik, R., et al., *Comparing the effects of scopolamine on operant and aggressive responses in squirrel monkeys.* Pharmacol Biochem Behav, 1975. 3(5): p. 739-48.
88. Guaiana, G., C. Barbui, and A. Cipriani, *Hydroxyzine for generalised anxiety disorder.* Cochrane Database Syst Rev, 2010(12): p. CD006815.
89. Iskandar, J. W., B. Griffeth, and C. Rubio-Cespedes, *Successful treatment with hydroxyzine of acute exacerbation of panic disorder in a healthy man: a case report.* Prim Care Companion CNS Disord, 2011. 13(3).
90. Kellner, M., *Experimental panic provocation in healthy man-a translational role in anti-panic drug development?* Dialogues Clin Neurosci, 2011. 13(4): p. 485-93.
91. Strohle, A., et al., *Effect of flumazenil in lactate-sensitive patients with panic disorder.* Am J Psychiatry, 1998. 155(5): p. 610-2.
92. MacKinnon, D. F., B. Craighead, and R. Hoehn-Saric, *Carbon dioxide provocation of anxiety and respiratory response in bipolar disorder.* J Affect Disord, 2007. 99(1-3): p. 45-9.
93. Kronenberg, G., et al., *In healthy volunteers responses to challenge with cholecystokinin tetrapeptide differ* between administration during REM and delta sleep. Depress Anxiety, 2001. 14(2): p. 141-4.
94. Gros, D. F., et al., *Psychometric properties of the State-Trait Inventory for Cognitive and Somatic Anxiety (STICSA): comparison to the State-Trait Anxiety Inventory (STAI)*. Psychol Assess, 2007. 19(4): p. 369-81.
95. Marteau, T. M. and H. Bekker, *The development of a six-item short-form of the state scale of the Spielberger State-Trait Anxiety Inventory (STAI)*. Br J Clin Psychol, 1992. 31 (Pt 3): p. 301-6.

The invention claimed is:
1. A method for treating symptoms of anxiety in a subject exhibiting alcohol addiction, alcohol withdrawal, drug addiction, and/or drug withdrawal, comprising administering to a subject in need thereof, a pharmaceutical composition consisting essentially of a therapeutically effective amount of a combination of at least one beta adrenergic receptor antagonist agent and/or pharmaceutically acceptable salts thereof, and at least one antiemetic muscarinic receptor antagonist agent and/or pharmaceutically acceptable salts thereof.
2. The method of claim 1, wherein the subject exhibits drug addiction and/or drug withdrawal, and wherein the drug is selected from opioids, opiates, and cocaine.
3. The method of claim 1, wherein the symptoms of anxiety are selected from the group consisting of tachycardia, increased blood pressure, palpitations, nausea, vomiting, mental anxiety (anxiousness), fear, avoidance, specific phobia, dyspnea, hyperventilation, migraine, headache, sweating, trembling, post-traumatic stress, alcohol dependence, drug dependence, restlessness, irritability, aggression, and delirium tremens.
4. The method of claim 1, wherein the at least one beta adrenergic receptor antagonist agent is selected from the group consisting of propranolol, atenolol, pindolol, nadolol, nebivolol, and/or pharmaceutically acceptable salts thereof, and *Eucommia* extract, and wherein the at least one antiemetic muscarinic receptor antagonist agent is selected from the group consisting of scopolamine, diphenhydramine, promethazine, meclizine, hydroxyzine, and/or pharmaceutically acceptable salts thereof.
5. The method of claim 1, wherein the at least one beta adrenergic receptor antagonist agent is propranolol, atenolol, pindolol, nadolol, nebivolol, and/or pharmaceutically acceptable salts thereof, in an amount of about 10 to 100 mg/dose for an adult, and wherein the at least one antiemetic muscarinic receptor antagonist agent is scopolamine, and/or pharmaceutically acceptable salts thereof, in an amount of about 0.05 to 1.0 mg/dose for an adult, and wherein the doses are lower for an adolescent or child.
6. The method of claim 1, wherein the pharmaceutical composition, when in liquid or semi-solid form, comprises at least one penetration-enhancing solvent selected from the group consisting of ethanol, glycerol, propylene glycol, ethoxydiglycol, and dimethylsulfoxide or, when in solid form, comprises at least one additional component selected from the group consisting of mannitol, a monosaccharide, a disaccharide, a bicarbonate buffer, a phosphate buffer, a binding agent, and a preservative.
7. The method of claim 1, wherein the pharmaceutical composition is in a form selected from the group consisting of a spray, an elixir, a solution, a suspension, an emulsion, a gel, a cream, a gum, a powder, a tablet, a capsule, a troche, a suppository, a pill, and a film, and wherein the pharmaceutical composition is administered to the animal, including a human, by a route of delivery selected from the group consisting of mucosal, sublingual, buccal, rectal, vaginal, nasal, parenteral, oral, and topical routes.
8. The method of claim 1, wherein the pharmaceutical composition is administered pro re nata (p.r.n.) to the animal, including a human, by a route of delivery selected from the group consisting of mucosal, sublingual, buccal, rectal, vaginal, nasal, and parenteral routes for rapid therapeutic effect commencing within 30 minutes or less, or by the oral route of delivery.
9. The method of claim 1, wherein the at least one beta adrenergic receptor antagonist agent exerts therapeutic effects on somatic cardiovascular symptoms, and the at least one antiemetic muscarinic receptor antagonist agent exerts therapeutic effects on somatic non-cardiovascular symptoms and/or central nervous system symptoms.
10. The method of claim 1, wherein administering the pharmaceutical composition to the subject in need thereof results in dryness of the mouth as a side effect of the antiemetic muscarinic receptor antagonist agent, and wherein this side effect deters continuous or daily administration of the pharmaceutical composition in a human.
11. The method of claim 1, wherein administration occurs when the subject anticipates symptoms of anxiety, or at the time of a trigger circumstance for the anxiety, or during symptoms of anxiety.
12. A pharmaceutical composition for pro re nata (p.r.n.) treatment of anxiety in a subject exhibiting alcohol addiction, alcohol withdrawal, drug addiction, and/or drug withdrawal, consisting essentially of a combination of at least one beta adrenergic receptor antagonist agent and/or pharmaceutically acceptable salts thereof, and at least one antiemetic muscarinic receptor antagonist agent and/or pharmaceutically acceptable salts thereof, together with one or more pharmaceutically acceptable excipients, wherein the at least one beta adrenergic receptor antagonist agent and the at least one antiemetic muscarinic receptor antagonist agent are combined in amounts therapeutically effective for p.r.n. symptomatic treatment of a subject and wherein the pharmaceutical composition is in a form for mucosal, sublingual, buccal, rectal, vaginal, nasal, or oral p.r.n. administration by a subject anticipating and/or experiencing symptoms of anxiety associated with alcohol addiction, alcohol withdrawal, drug addiction, and/or drug withdrawal.
13. The pharmaceutical composition of claim 12, wherein the form is a liquid or semi-solid form comprising at least one penetration-enhancing solvent selected from the group consisting of ethanol, glycerol, propylene glycol, ethoxydiglycol, and dimethylsulfoxide, or wherein the form is a solid form comprising at least one component selected from the group consisting of mannitol, a monosaccharide, a disaccharide, a bicarbonate buffer, a phosphate buffer, a binding agent, and a preservative.
14. The pharmaceutical composition of claim 12, wherein the at least one beta adrenergic receptor antagonist agent is selected from the group consisting of propranolol, atenolol, alprenolol, acebutolol, betaxolol, bisoprolol, bucindolol, celiprolol, nadolol, sotalol, esmolol, carteolol, carvedilol, mepindolol, nebivolol, oxprenolol, penbutolol, pindolol, landiolol, metoprolol, timolol, labetolol, and/or pharmaceutically acceptable salts thereof, and *Eucommia* extract, an active pharmaceutical ingredient of *Eucommia*, and/or pharmaceutically acceptable salt thereof.
15. The pharmaceutical composition of claim 12, wherein the at least one antiemetic muscarinic receptor antagonist agent is selected from the group consisting of scopolamine, diphenhydramine, meclizine, buclizine, cyclizine, hydroxyzine, pirenzepine, benztropine (benzatropine), hyoscyamine, butylscopolamine, methylscopolamine, doxylamine, promethazine, trihexyphenidyl, orphenadrine, and/or pharmaceutically acceptable salts thereof.

16. The pharmaceutical composition of claim 12, wherein the at least one beta adrenergic receptor antagonist agent is selected from the group consisting of propranolol, atenolol, pindolol, nadolol, nebivolol, labetolol, and/or pharmaceutically acceptable salts thereof, and *Eucommia* extract, and wherein the at least one antiemetic muscarinic receptor antagonist agent is selected from the group consisting of scopolamine, diphenhydramine, cyclizine, doxylamine, orphenadrine, meclizine, hydroxyzine, promethazine, and/or pharmaceutically acceptable salts thereof.

17. The pharmaceutical composition of claim 12, wherein the at least one beta adrenergic receptor antagonist agent and/or pharmaceutically acceptable salts thereof, is in an amount of about 10 to 100 mg/dose, and wherein the at least one antiemetic muscarinic receptor antagonist agent and/or pharmaceutically acceptable salts thereof, is scopolamine in an amount of about 0.05 to 1.0 mg/dose, and/or is not scopolamine in an amount of about 10 to 100 mg/dose.

18. The pharmaceutical composition of claim 12, wherein the at least one antiemetic muscarinic receptor antagonist agent is scopolamine, and wherein the at least one beta adrenergic receptor antagonist agent and the at least one antiemetic muscarinic receptor antagonist agent are combined in amounts therapeutically effective for p.r.n. symptomatic treatment in a ratio in a range of 150:1 to 40:1 (beta adrenergic receptor antagonist agent:antiemetic muscarinic receptor antagonist agent).

* * * * *

UNITED STATES PATENT AND TRADEMARK OFFICE
CERTIFICATE OF CORRECTION

| | |
|---|---|
| PATENT NO. | : 9,616,052 B2 |
| APPLICATION NO. | : 15/345896 |
| DATED | : April 11, 2017 |
| INVENTOR(S) | : Thomas P. Dooley |

Page 1 of 1

It is certified that error appears in the above-identified patent and that said Letters Patent is hereby corrected as shown below:

Page 2, Column 1, Other Publications: Reference BRESLAU, N. et al.: "Headaches" should read --Headache--.

Page 3, Column 2, Other Publications: Reference MACKINNON, Dean, F., et al.: "anxiety" should read --anxiety and respiratory--.

Page 3, Column 2, Other Publications: Reference MANSUR, A.P. et al.: "Medical" should read --Medical and Biological--.

Page 3, Column 2, Other Publications: Reference PITMAN, Roger, K., et al.: "142" should read --192--.

Signed and Sealed this
Twenty-third Day of May, 2017

Michelle K. Lee
*Director of the United States Patent and Trademark Office*